(12) United States Patent
O'Hara

(10) Patent No.: US 9,283,084 B1
(45) Date of Patent: Mar. 15, 2016

(54) SPINAL FUSION CAGE AND VERTEBRAL BODY CLAMP

(71) Applicant: Thomas E. O'Hara, Troy, MI (US)

(72) Inventor: Thomas E. O'Hara, Troy, MI (US)

( * ) Notice: Subject to any disclaimer, the term of this patent is extended or adjusted under 35 U.S.C. 154(b) by 310 days.

(21) Appl. No.: 13/949,782

(22) Filed: Jul. 24, 2013

Related U.S. Application Data

(60) Provisional application No. 61/675,004, filed on Jul. 24, 2012.

(51) Int. Cl.
*A61F 2/44* (2006.01)

(52) U.S. Cl.
CPC . *A61F 2/44* (2013.01); *A61F 2/447* (2013.01); *A61F 2/4455* (2013.01)

(58) Field of Classification Search
CPC .......... A61F 2/44; A61F 2/4455; A61F 2/447
See application file for complete search history.

(56) References Cited

U.S. PATENT DOCUMENTS

| | | | | |
|---|---|---|---|---|
| 3,426,364 A * | 2/1969 | Lumb | | 623/17.15 |
| 4,289,123 A * | 9/1981 | Dunn | | 606/250 |
| 4,863,476 A * | 9/1989 | Shepperd | | 623/17.15 |
| 5,390,683 A * | 2/1995 | Pisharodi | | 128/898 |
| 5,658,335 A * | 8/1997 | Allen | | 623/17.16 |
| 5,782,832 A * | 7/1998 | Larsen et al. | | 623/17.11 |
| 5,800,550 A * | 9/1998 | Sertich | | 623/17.16 |
| 5,951,553 A * | 9/1999 | Betz et al. | | 606/279 |
| 6,102,950 A * | 8/2000 | Vaccaro | | 623/17.16 |
| 6,120,503 A * | 9/2000 | Michelson | | 606/86 A |
| 6,159,211 A * | 12/2000 | Boriani et al. | | 606/279 |
| 6,179,873 B1 * | 1/2001 | Zientek | | 623/17.11 |
| 6,264,655 B1 * | 7/2001 | Pisharodi | | 606/247 |
| 6,325,827 B1 * | 12/2001 | Lin | | 623/17.16 |
| 6,494,883 B1 * | 12/2002 | Ferree | | 606/247 |
| 6,821,298 B1 * | 11/2004 | Jackson | | 623/17.15 |
| 7,128,760 B2 * | 10/2006 | Michelson | | 623/17.15 |
| 7,731,751 B2 * | 6/2010 | Butler et al. | | 623/17.11 |
| 8,070,813 B2 * | 12/2011 | Grotz et al. | | 623/17.11 |
| 8,523,946 B1 * | 9/2013 | Swann | | 623/17.16 |
| 8,795,335 B1 * | 8/2014 | Abdou et al. | | 606/247 |
| 2002/0106393 A1 * | 8/2002 | Bianchi et al. | | 424/423 |
| 2002/0138146 A1 * | 9/2002 | Jackson | | 623/17.15 |
| 2003/0187436 A1 * | 10/2003 | Bolger et al. | | 606/61 |
| 2005/0071008 A1 * | 3/2005 | Kirschman | | 623/17.11 |
| 2005/0101960 A1 * | 5/2005 | Fiere et al. | | 606/72 |
| 2006/0074490 A1 * | 4/2006 | Sweeney | | 623/17.15 |
| 2007/0027416 A1 * | 2/2007 | Rapp | | 602/5 |
| 2007/0270968 A1 * | 11/2007 | Baynham et al. | | 623/17.11 |
| 2010/0185289 A1 * | 7/2010 | Kirwan et al. | | 623/17.11 |
| 2011/0118840 A1 * | 5/2011 | Huntsman et al. | | 623/17.11 |
| 2011/0172774 A1 * | 7/2011 | Varela | | 623/17.16 |
| 2011/0208311 A1 * | 8/2011 | Janowski | | 623/17.16 |
| 2011/0230971 A1 * | 9/2011 | Donner et al. | | 623/17.16 |
| 2011/0288645 A1 * | 11/2011 | Braddock et al. | | 623/17.16 |
| 2012/0265259 A1 * | 10/2012 | LaPosta et al. | | 606/86 A |

(Continued)

*Primary Examiner* — Christian Sevilla
(74) *Attorney, Agent, or Firm* — Emch, Schaffer, Schaub & Porcello Co., L.P.A.

(57) ABSTRACT

The invention is directed to a fusion cage designed for lateral placement. The cage is roughly rectangular in shape and hollow on the inside to accommodate bone graft material. Staples can be incorporated into the fusion cage to assist in securing the cage in position in the spine. A rod can be attached to the staples to assist in positioning the staples. A cable can be attached to the rod to assist in positioning the cage and to assist in positioning the spine. A lateral plate can be used with the cage to further assist in maintaining the cage and the spine in the desired position.

30 Claims, 29 Drawing Sheets

(56) References Cited

U.S. PATENT DOCUMENTS

2013/0053891 A1* 2/2013 Hawkins et al. ............. 606/264
2013/0073044 A1* 3/2013 Gamache .................. 623/17.16
2013/0245767 A1* 9/2013 Lee et al. .................. 623/17.16
2013/0297024 A1* 11/2013 Khurana .................... 623/17.12
2014/0094918 A1* 4/2014 Vishnubholta et al. .... 623/17.16
2014/0121773 A1* 5/2014 Patel et al. ................ 623/17.16

* cited by examiner

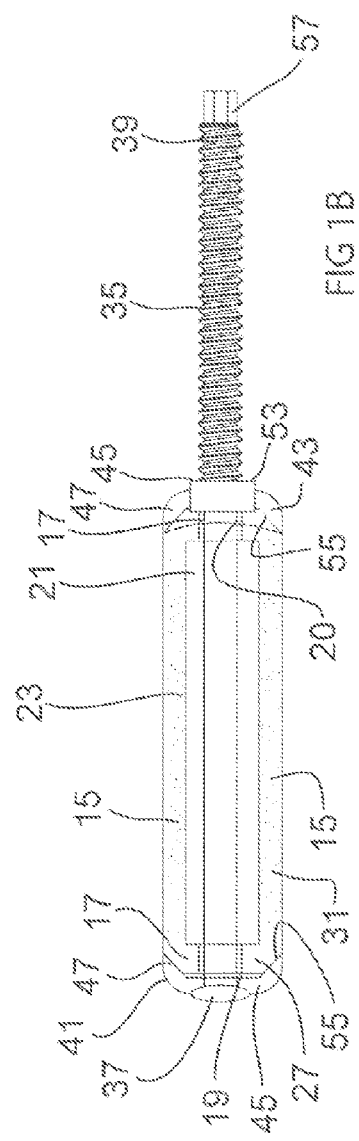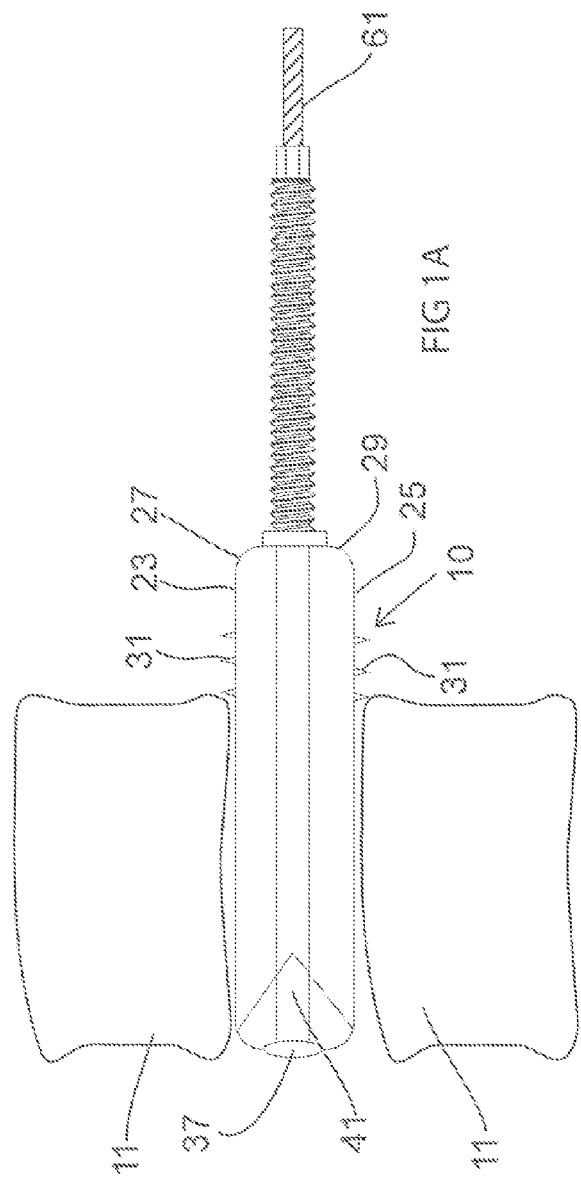

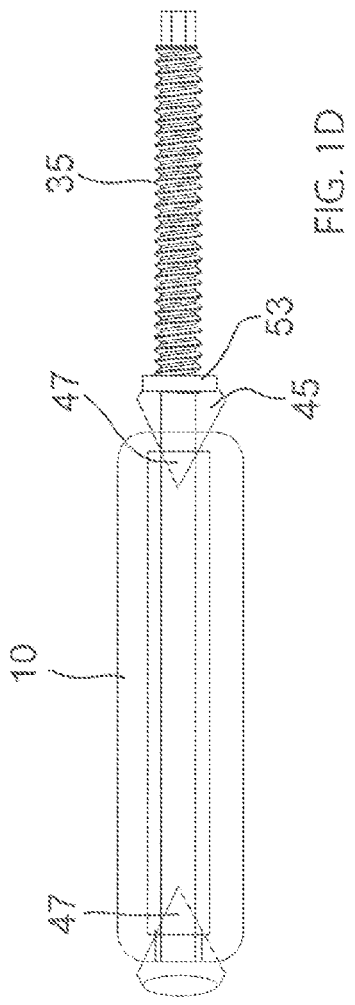
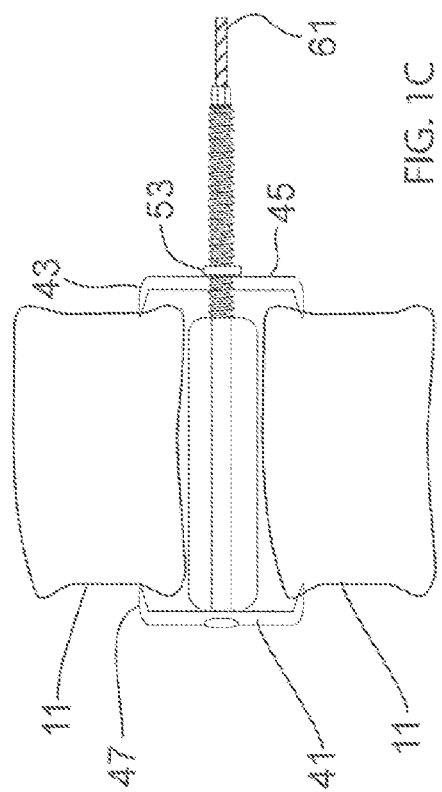

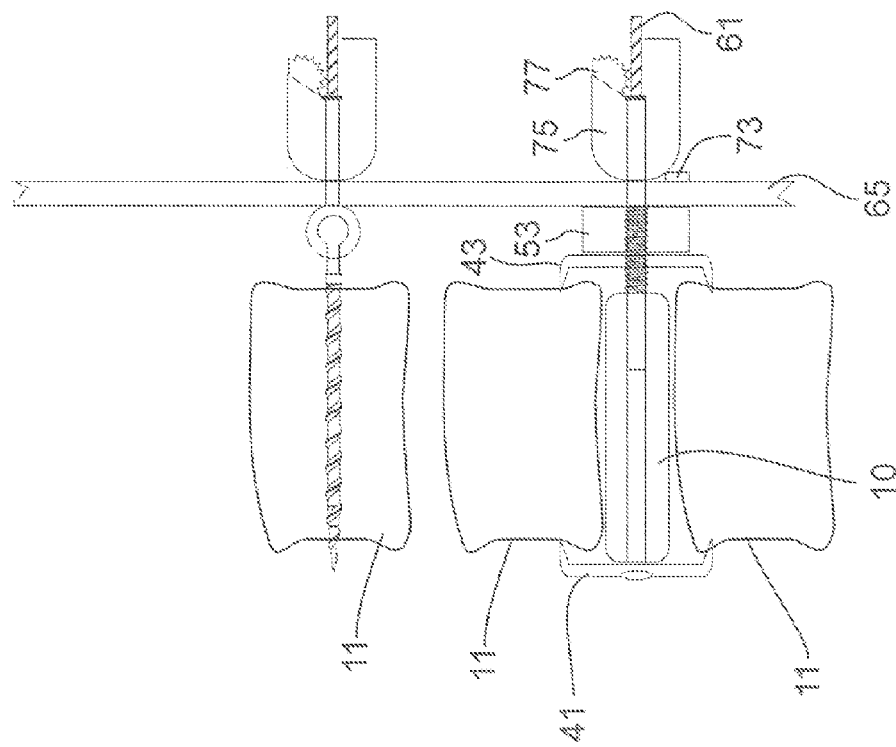

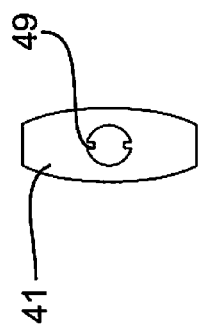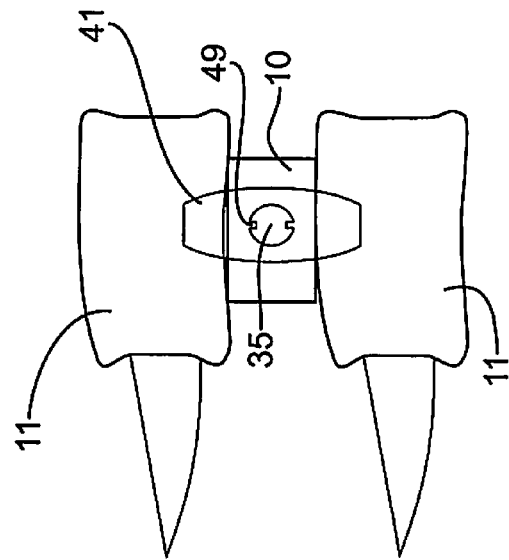

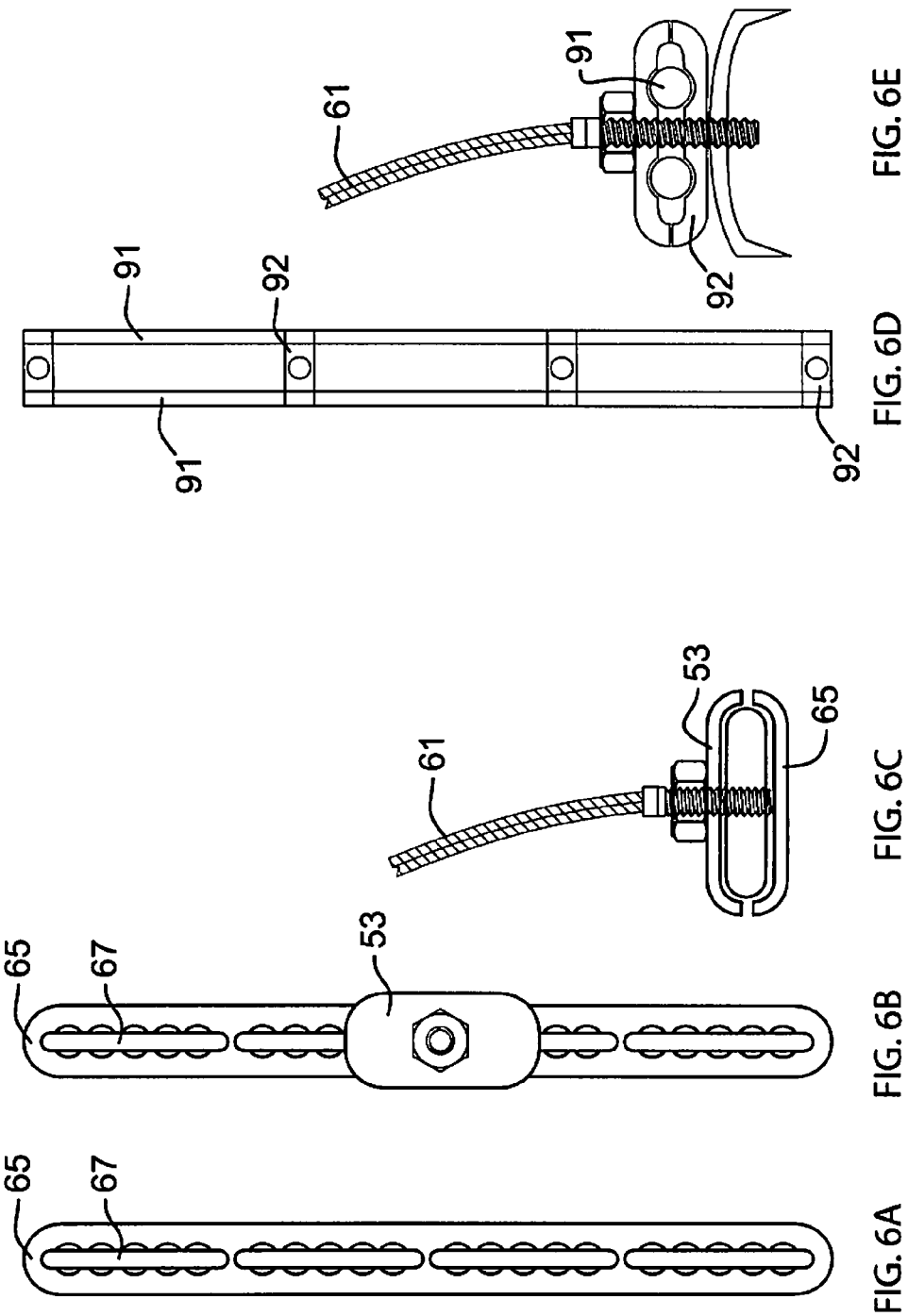

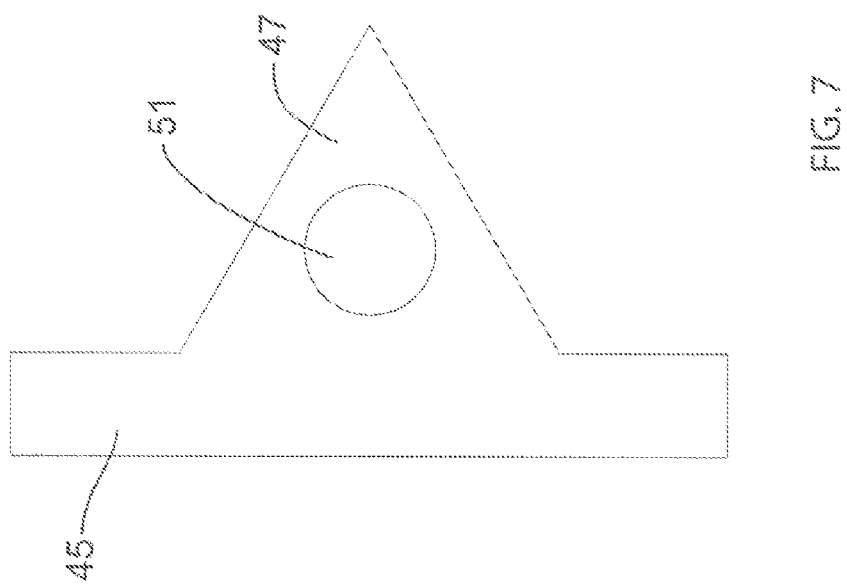

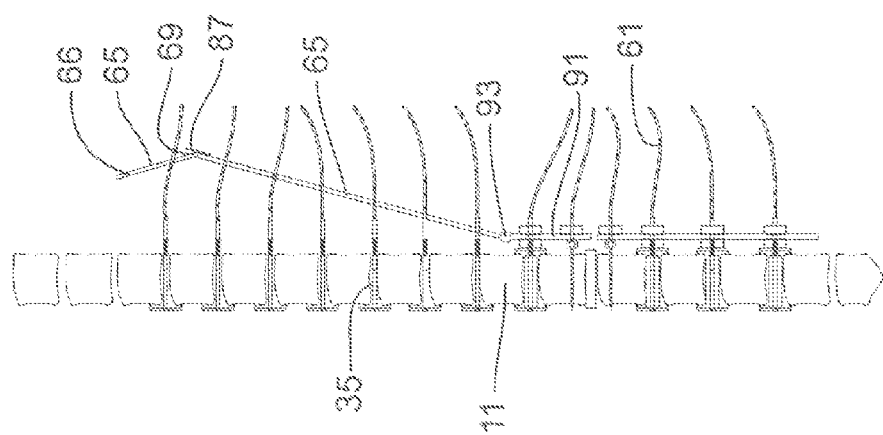

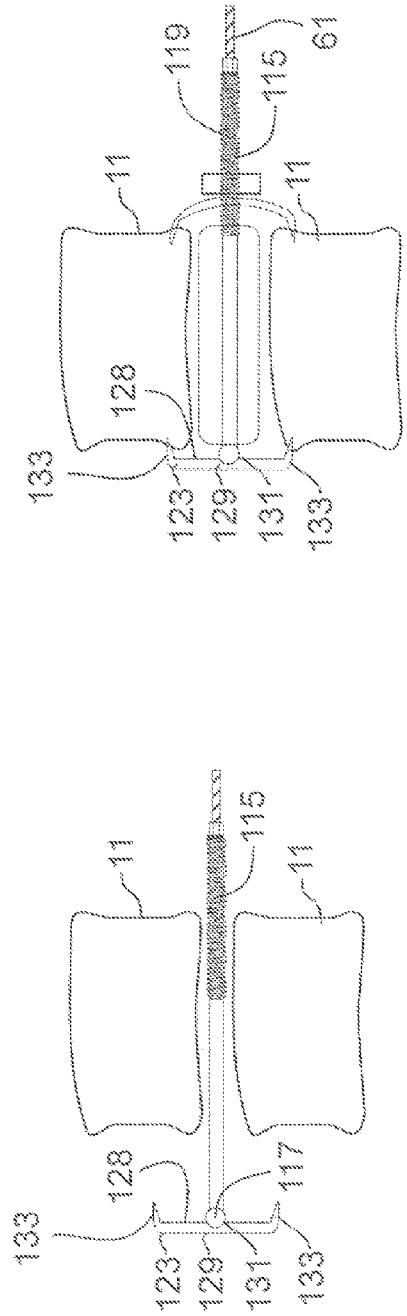
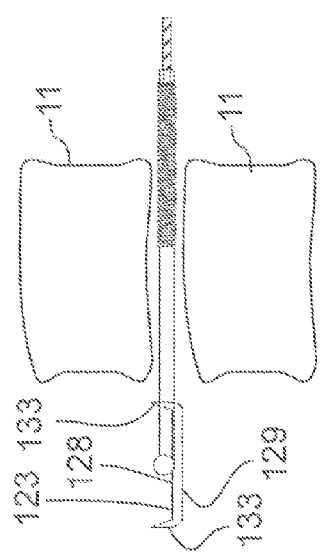
FIG. 13
FIG. 14
FIG. 15

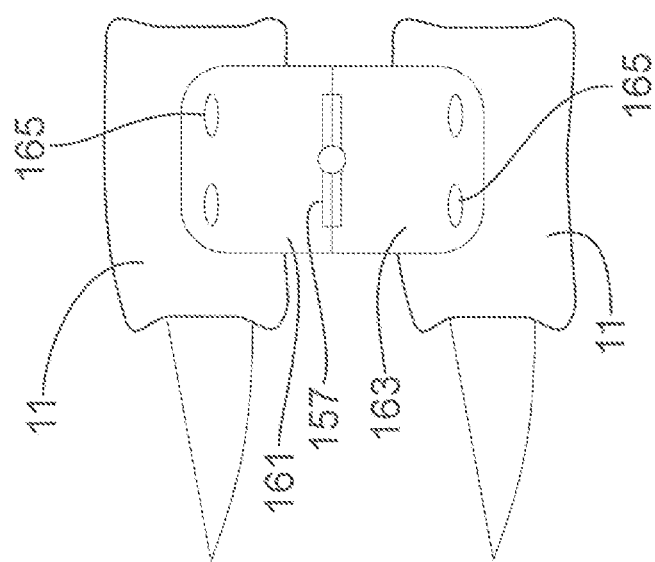

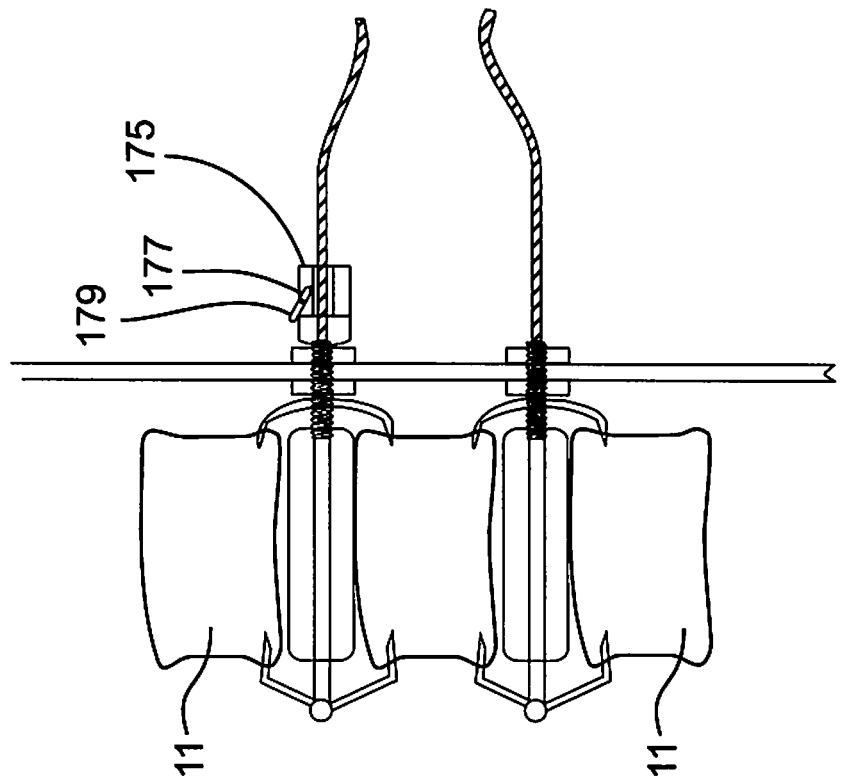
FIG. 21C
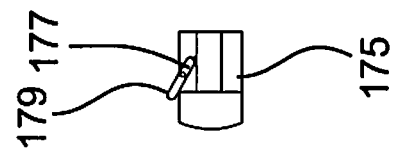
FIG. 21B
FIG. 21D

SPINAL FUSION CAGE AND VERTEBRAL BODY CLAMP

CROSS REFERENCE TO RELATED APPLICATIONS

This application claims the benefit of U.S. provisional patent application Ser. No. 61/675,004 filed Jul. 24, 2012.

BACKGROUND OF THE INVENTION

Inter-body fusion is a commonly used technique to permanently attach vertebrae together to stabilize the spine in order to relieve nerve compression, stop pain, correct subluxation, correct scoliosis and repair damage from fractures and tumors. Typically the fusion is performed by removing disk material and damaged bone from between the vertebral bodies, putting a spacer or "fusion cage" between the vertebra to maintain the space between them and adding bone graft material into which new bone can grow to "fuse" the vertebrae together. An inter-body fusion of the lumbar spine can be performed anteriorly, posteriorly, inferiorly and laterally. Anterior approaches are complicated by having to work around the abdominal cavity and large blood vessels such as the aorta and vena cava. The anterior longitudinal ligament must be sacrificed in this approach and scoliosis cannot be effectively corrected because the lateral walls of the disk annulus cannot be released (cut) to correct lateral curvature of the spine related to degenerative changes in a disk. A posterior approach is compromised by the dural sac and spinal nerves. The posterior longitudinal ligament is often weakened and scoliosis cannot be corrected because the lateral walls of the annulus cannot be released. An inferior or "pre-sacral" approach is limited to the L4-L5 and L5-S1 disk levels and cannot be used to correct any significant amount of scoliosis. The lateral (direct lateral or extreme lateral) approach is compromised by the lumbar nerve roots but the annulus of the disk can be cut on each side, the anterior and posterior longitudinal ligaments preserved and a large inter-body cage can be placed to correct scoliosis or a lateral tilt of the spine. Inter-body fusions of the thoracic spine are done through the chest (transthoracic) or posterior laterally. The transthoracic approach is compromised by having to collapse a lung and work between the ribs. A posterolateral approach is compromised by the spinal cord and nerve roots. All of these approaches to the lumbar and thoracic spine for inter-body fusions are currently being done with minimally invasive techniques to minimize skin incisions and more importantly muscle damage.

Inter-body fusions are generally reinforced with plates or rods secured with bone screws. Pedicle screws and rods are most commonly used to reinforce inter-body fusions and to perform extensive corrections of lumbar and thoraco-lumbar scoliosis. Although one or two vertebral level pedicle screw and rod instrumentation can be reliably performed with minimally invasive techniques, more lengthy constructs generally require open operations to insert the screws and rods, especially if there is curvature of the spine. The advantages of anterior, inferior and lateral approaches for lumbar inter-body fusions and the advantages of trans-thoracic inter-body fusions are compromised by having to do a second operation from the back to reinforce the inter-body fusions. A lateral plate can be reliably placed to re-enforce a single level lateral lumber inter-body fusion, multiple level lumbar lateral plates are not currently feasible necessitating additional posterior pedicle screw and rod instrumentation. Lateral plates or rods have been placed over several levels in the thoracic spine via a trans-thoracic approach but not over longer distances.

Considering the advantages of lateral inter-body fusions in the lumbar and thoracic areas a multi-level lateral system to stabilize the spine in these areas would be of great utility to allow multi-level inter-body fusions of the thoracic and/or lumbar spine without an additional open posterior operation.

SUMMARY OF THE INVENTION

The invention is directed to a fusion cage designed for lateral placement. The cage is roughly rectangular in shape and hollow on the inside to accommodate bone graft material. Staples connected by a rod can be incorporated into the fusion cage at each end to clamp the vertebral body above and below the cage in position to stabilize them while the fusion develops. A cable can be attached to the end of the rod to assist in positioning lock nuts and a lateral plate on the rod and also to put traction on the cage, vertebral body clamp and vertebrae to pull them into alignment and correct scoliosis. A lateral plate attached to the cage, to other cages, to screws placed in vertebrae, to disk supports or to artificial disks in the thoracic and/or lumbar area of the spine to can be used to maintain alignment and correct scoliosis. Motion preservation devices including an artificial disk are included in the design as well as a large cage using shims and vertebral body clamps for use in corpectomies.

Other objects and advantages of the present invention will become apparent to those skilled in the art upon a review of the following detailed description of the preferred embodiments and the accompanying drawings.

BRIEF DESCRIPTION OF THE DRAWINGS

FIG. 1A is a side elevational view of the spinal fusion cage of the present invention.
FIG. 1B is a top view.
FIG. 1C is a side elevational view.
FIG. 1D is a top view.
FIG. 4 is a side elevational view of the spinal fusion cage.
FIG. 5A is a partial side elevational view.
FIG. 5B is a partial side elevational view.
FIG. 6A is a partial side elevational view of the staple or lateral plate.
FIG. 6B is a partial side elevational view of another feature of the lateral plate.
FIG. 6C is a partial top view.
FIG. 6D is a partial side elevational view of another feature of the lateral plates.
FIG. 6E is a partial side elevational view.
FIG. 7 is a partial side elevational view of a staple or lateral plate.
FIG. 12A is a side elevational view of an additional feature of the invention.

FIG. 13 is a side elevational view of another feature of the invention.

FIG. 14 is a side elevational view of the staple of FIG. 13.

FIG. 15 is a side elevational view.

FIG. 19 is an end view of the staple of FIG. 17.

FIG. 21A is a side elevational view of another feature of the invention.

FIG. 21B is a partial side elevational view.

FIG. 21C is a partial end view.

FIG. 21D is a partial end view.

DETAILED DESCRIPTION OF THE PREFERRED EMBODIMENT(S)

Figure 2B:
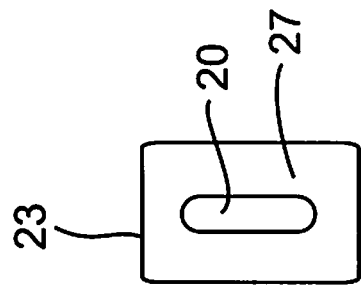
FIG. 2B is a partial right side end view.

Intervertebral Body Fusion Cage and Vertebral Body Clamp

The proposed system involves a laterally placed fusion cage made of PEEK, metal, cortical autologous (donor) bone or some other material with an integral metal pronged vertebral body bone clamp. The cage is roughly rectangular in shape, hollow on the inside to allow placement of bone graft material in it. The top and bottom edges of the cage are serrated to help hold it in position in the inter-space where the center of the disk has been removed. Radio opaque markers would be incorporated into the cage. Various lengths of cages would be produced to accommodate various widths of the vertebral bodies as well as cages taller in the front than the back or taller in the back than front to allow for a normal lordotic or kyphotic curvature of the fused segment. Cages would also be produced that are taller on one side or the other to correct lateral curvature of the spine (scoliosis) resulting from deformity of the vertebral bodies rather than the disk. A round metal, probably titanium, rod runs through a round hole in one of the small sides of the cage and through a slit on the opposite side. The slit allows the rod to align with a lateral plate. On the side of the cage with the round hole, the rod is loosely but strongly attached to a metal plate with two sharp prongs on each side directed inward, toward the center of the cage. These prongs would have one or more holes or be covered with hydoxyapatite for bone ingrowth. The connection of the plate and rod would be "keyed" so that the plate could be rotated with the rod. Staples that are hinged or folded to the rod can also be utilized with the invention. The staples can also have additional prongs to provide additional stabilization of the vertebrae above and below the cage. The plate would form a "cap" on the end of the cage and would be rounded to help smoothly guide the cage into the disk space. The prongs would be recessed into indentations on each side of the cage when the cage is placed in the disk space. A cable of Sulene PET with a radio opaque marker, stainless steel, titanium or some other material is attached to the end of the rod opposite the plate. The cable could have a screw type connection to the rod or be swedged on.

The disk space would be prepared by cutting away the annulus of the disk on each side, removing the nucleus pulpous and removing the cartilaginous end plates using specially designed tools. The cage would then be placed (gently impacted) into the disk space with fluoroscopic control, or using other imaging techniques (such as an "O" arm). Pressure is placed on the rod to advance the "cap" through a previously made opening in the annulus of the disk on the far side. The rod is then rotated forty five to ninety degrees. A second staple with prongs facing the bone is then passed down the cable and placed over the rod on the opposite side from the first plate. This portion of the rod is also "keyed" to align this plate with the first. A locking nut placed down over the cable is tightened down to "clamp" the vertebral bodies between the two plates forcing the sharp prongs into the bone. At this point the two vertebral bodies should be in good alignment as a result of the large fusion cage, fixed in position with the bone clamp and have bone graft material in the center of the cage to induce an inter-body fusion. This procedure is done in the lumbar area using a lateral retractor system and magnification. In the thoracic area it is done with thorascopic equipment and technique.

With the first level completed, additional levels can be done, generally working from the ends to the center of a lateral curve allowing the cages in the disk spaces to gradually correct the scoliosis. If a disk is severely degenerated preventing the placement of a cage, or if a disk space is damaged in the process of inserting a cage, then bone screws with poly-axial heads and cables attached to them can be placed in the vertebral body above and below the bad disk space and bone graft material can simply be placed into the disk space. If lateral traction for alignment is needed at a disk space without a fusion, then a rod with a folding plate and cable attached to the other end can be placed through the disk. The folding head would expand on the other side and with traction placed on the cable in a fashion to be described shortly, the prongs on the ends of the plate would be forced into the vertebral bodies and the plate, rod and cable can then be used to pull the vertebral bodies laterally.

Once all of the inter-body devices and bone screws are in place, the cables, which have been kept in order with a clip holding the distal ends, are placed in order in a lateral plate made of titanium or stainless steel. The plate is pre-shaped with a standard lordotic or kyphotic curvature for the length. Spacers can be positioned on the cables and disposed adjacent the vertebrae. The spacers position the plate away from the vertebrae so that it does not compress muscle adjacent to the spine. The plate has a hollow center running almost its entire length so that it is essentially an elongated oval. The inner edges are scalloped. The plate, depending on its length, may have one or more hinges allowing the plate to fold toward the spine and open away from it. A locking mechanism to keep the plate from opening more than one hundred eighty degrees would be on the side away from the spine. The plate may also have one or more hinge points to allow for adjustments for lordotic and kyphotic curvatures. The lumbar plate may have a "pocket" with a locking mechanism to accept the bottom end of a lateral thoracic plate placed through the diaphragm for thoraco-lumbar constructs. In the lumbar area the folded (if necessary) plate is placed through the incision previously made for the retractor. The folded lateral plate is opened and slid down the cables to the threaded posts on the clamp rods, threaded posts on the tops of the vari-angle bone screws or the threaded rods on the lateral pullers. If the rods or posts go right into the plate, then a lock nut in a canulated, articulated socket wrench can be placed down over the cable to the threaded rod or post and tightened down on it. The bottom of the lock nut and the top of the lock nut for the bone clamp are rounded to fit in the scallops on the inner edges of the lateral plate. If there is still some scoliosis and the rods or posts won't go into the plate, then a screw/tensioning device can be used with the cables and an articulated cable puller to pull the rods of the bone clamps or posts of the bone screws into the lateral plate to correct any residual scoliosis. The screw/tensioning devices have a metal tube with a cable locking device on the distal end and a bolt on the other end that turns freely around the tube and can be tightened down on the rod or post. With the bone clamps, bone screws and pulling devices secured to the lateral plate, the cables can be cut or unscrewed. The same procedure would be followed in the thoracic area except that thorascopic procedures and equipment are used. Several folds may be necessary in the lateral plate. Articulations in the thoracic and lumbar plates can be used to correct for greater or lesser than normal lordosis or kyphosis. The instrumentation would include a slap hammer type extractor to reposition a cage, an emergency release device for the cable to allow repositioning, articulated and canulated socket wrenches with a torque device, a cable tensioner and a cable cutter if a cable material such as Sulene PET is used. The ability to place a thoracic plate through the diaphragm and connect it to a lumbar plate allows for staging of a large thoraco-lumbar fusion into two operations or allows a surgeon to work in the thorax while another works in the lumbar area. With this minimally invasive system there is minimal muscle trauma (none to the posterior muscles) and skin incisions are quite small.

Figure 2A:
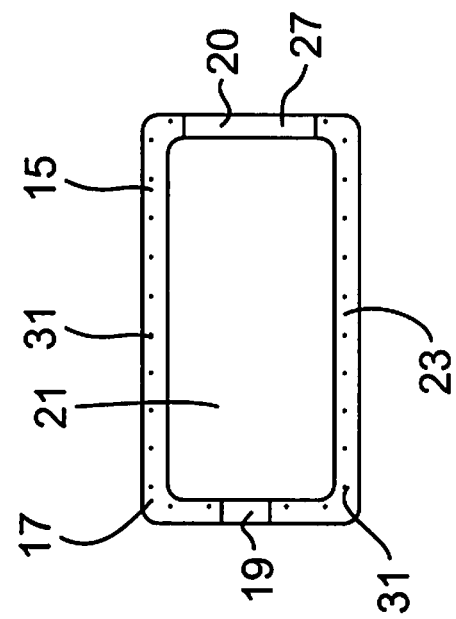
FIG. 2A is a partial top view of the cage.
Figure 2C:
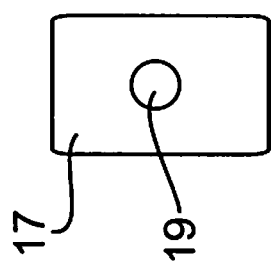
FIG. 2C is a partial left side end view.

The spinal fusion cage 10 is shown in FIG. 2. The cage would be made of a plastic such as PEEK, metal such as trabecular tantalum, autologous (donor) cortical bone or other suitable materials that are well known in the art. The cage has opposed sidewalls 15 that are disposed in a substantially parallel relationship. The cage 10 also has opposed end walls 17 that are disposed in substantially parallel relationship. The end walls 17 are connected to the two sidewalls 15 to form the spinal fusion cage. The interior of the spinal fusion cage 10 defines a cavity 21 that extends between the sidewalls 15 and the end walls 17. Bone graph material can be positioned in the cavity 21 as is well known in the art. An aperture 19 is positioned in one end wall 17 and a slit 20 is positioned in the opposite end wall. The slit 20 extends across most of the width of the one end wall and is considerably wider than the aperture 19 of the cage 10. The apertures 19 and the slits 20 are disposed to be in general alignment with each other. The sidewalls 15 define an upper surface 23 and lower surface 25. The end walls 17 define and upper edge 27 and a lower edge 29. The upper and lower surfaces of the sidewalls 15 and the upper and lower edges of the end walls 17 can contain serrations 31 or otherwise be roughened to assist in holding the cage in position when in use.

Figure 3A:
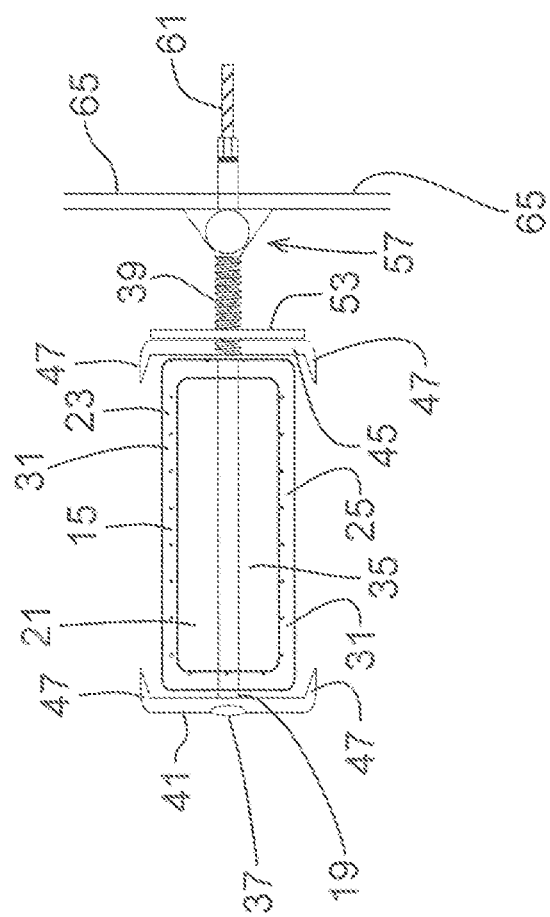
FIG. 3A is a top view of the invention.
Figure 3B:
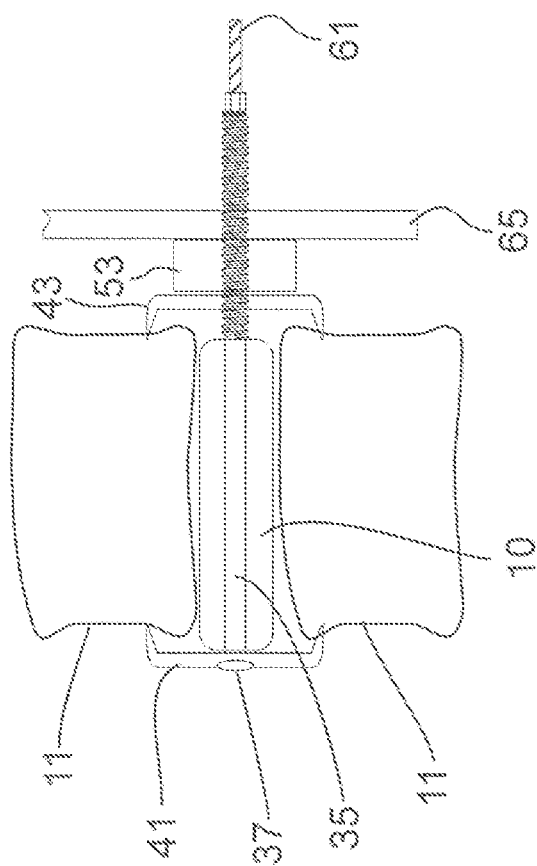
FIG. 3B is a side elevational view.

A threaded rod 35 is positioned in the aperture 19 and the slit 20 located in the end walls 17 as shown in FIGS. 1,2,3. The threaded rod has a first end 37 and a second end 39. A first staple or lateral plate 41 is positioned on the portion of the first end 37 of the threaded rod 35 that extends beyond the end wall 17 of the cage 10. A second staple or lateral plate 43 is positioned adjacent the second end 39 of the threaded rod 35. The second staple or lateral plate 43 is positioned on the portion of the threaded rod that extends beyond the end wall 17 of the cage 10. The first staple 41 and second staple 43 are disposed so that they are on the side of the end walls 17 that are spaced apart from the cavity 21 formed in the interior of the cage 10. The first and second staples have a base 45 and a projection 47 that extend from each end of the base 45. The projections 47 extend in the same direction from the base 45 and the projections are disposed in substantially parallel relationship. The projections 47 on the first staple 41 and the second staple 43 are disposed so that the projections extend in a direction towards the cage 10. The projections 47 are further disposed so that they extend along the sidewalls 15 of the cage 10. The projections 47 can have a hole 51 that extends through the projections. The holes 51 are disposed to facilitate bone growth through the holes. The first and second staples are secured to the threaded rod 35 or held in place by a key 49 or other suitable means on the threaded rod 35. The placement of the first and second staples 41, 43 on the threaded rod 35 allows the staples to be rotated to a different orientation by the rotation of the threaded rod 35. The threaded rod is rotated using a drive head that could be hex shaped or in another form. The second end of the rod with the drive head can be straight 1A or of a vari-angle design 3A. The rod is rotated with a driver that is placed on the drive head of the rod. A flexible cable 61 is operatively connected to the second end 39 of the threaded rod 35. The flexible cable can be made of a sulene PET with a radio opaque marker, stainless steel, titanium or other suitable materials. The cable has a length sufficient to allow it to extend from the patient when the spinal fusion cage is placed in position in the spine of the patient. A lock nut is placed on the cable and slid down it into position adjacent the second end 39 of the threaded rod. The lock nut is disposed to engage the threads on the threaded rod 35. The lock nut 53 is also disposed to engage a second staple 43 positioned on the second end 39 of the threaded rod 35. The lock nut 53 can be advanced in a direction towards the second staple 43 using socket tool to move the second staple in a direction towards the cavity 21 and the cage 10. Sidewalls 15 of the cage 10 have indentations 55 where the projections 47 on the first and second staples are positioned when the final fusion cage 10 is in the insertion orientation.

In operation the spinal fusion cage 10 is positioned between adjacent vertebrae 11 to fill the space where a disc has been removed. When the cage has been properly positioned the threaded rod 35 is rotated to bring the projections 47 of the first staple 41 and the second staple 43 from the indentations 55 located on the sidewalls 15 of the cage 10. The threaded rod is rotated until the projections 47 on the first and second staples are in alignment with the vertebrae 11 positioned above and below the space where the spinal fusion cage 10 has been inserted in the spine. The threaded rod 35 is provided with a key 49 that engages the first and second staples that cause these staples to rotate when the threaded rod is rotated to move the first and second staple into position with the adjacent vertebrae. The flexible cable 61 extends from the threaded rod 35 to exterior of the patient. A lock nut 53 can be positioned on the threaded rod 35 or advanced along the flexible cable 61 until the lock nut is in alignment with and advanced onto the threaded rod. The lock nut is then rotated on the threaded rod 35 until the lock nut provides sufficient force against the second staple 43 and along the threaded rod 35 to advance the projections 47 on the first and second staples into the bone on the vertebrae 11 positioned above and below the spinal fusion cage 10. The lock nut 53 is advanced along the threaded 35 until the first and second staples are securely imbedded into the vertebrae 11 above and below the spinal fusion cage 10. Once the first and second staples are secured into the vertebrae 11 the spinal fusion cage 10 will be held in position between the vertebrae 11 above and below the cage. The serrations 31 on the edges of the sidewalls 15 and end walls 17 of the cage will also assist in holding the spinal fusion cage in the desired position.

FIGS. 13-16 show an additional feature that can be used with the present invention. A bone clamp 110 is disclosed that is similar to the threaded rod 35 and first staple 41 previously described. The bone clamp 110 has an elongated rod 113 having a threaded portion 115. The elongated rod has a first end 117 and a second end 119. The first end 117 of the elongated rod 113 has a pivot bar 123 that is joined to the elongated rod 113 and an orientation that is substantially perpendicular to the longitudinal axis of the elongated rod. A flexible cable 61 is attached to the second end 119 of the elongated rod 113 in the manner previously described herein.

A plate 127 is pivotally attached to the pivot bar 123 on the first end 117 of the elongated rod 113. The plate 127 has a pair of journals 131 that are positioned on the first surface 128 of the plate. The second surface 129 of the plate 127 is positioned in opposed relationship with the first surface. The ends of the pivot bar 123 are disposed to engage the journals 131 to pivotally mount the plate 127 on the elongated rod 113. A projection 133 is positioned on the first surface 128 of the plate 127. The projection extends from the plate 127 in a direction that is substantially perpendicular to the first surface of the plate. In practice it has been found desirable to have projections 131 positioned on each corner of the first surface 128 of the plate 127. The projections 131 are disposed on the plate to allow the projections to engage the vertebrae 11 in a patient's spine.

The bone clamp 110 is positioned with the plate 127 in a pivoted orientation where the first surface 128 of the plate is positioned in an orientation that is substantially parallel to the longitudinal axis of the elongated rod 113. In this position the plate and the elongated rod can be inserted in the space between adjacent vertebrae 11 in the spine of a patient. When the plate is entirely through the space between the adjacent vertebrae, the plate 127 can be rotated so that the first surface 128 of the plate is in substantially perpendicular relationship to the elongated rod 113. When the plate 127 is in the second position where it is substantially perpendicular to the longitudinal axis of the elongated rod the projections 131 are in position to engage the vertebrae 11 on either side of the disc space through which the bone clamp 110 was advanced. The cable 61 can be tensioned to hold the bone clamp 110 in the desired position. In addition, a fusion cage 10, second staple 43 and lock nut 53 can be positioned on the elongated rod 113 in the manner previously described. The lock nut 53 can be used to place tension on the plate 127 and the second stable 43 to cause the projections 131 on the plate 127 and the projections 47 on the second stable 43 to advance into the bone and the adjacent vertebrae 11. The bone clamp 110 can be used in the same manner as the threaded rod 35 and first stable 41 previously described.

Figure 17A:
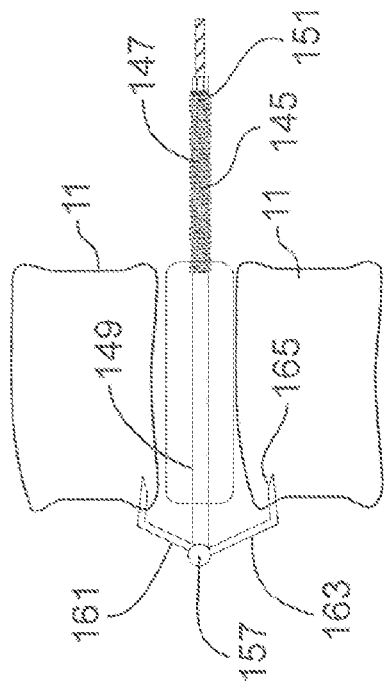
FIG. 17A is a side elevational view of an additional feature of the invention.
Figure 17B:
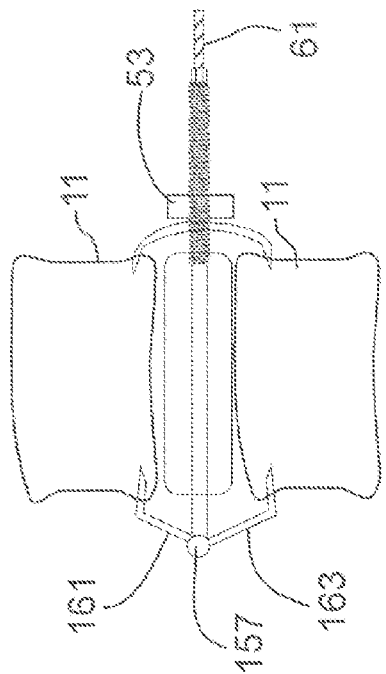
FIG. 17B is a side elevational view.
Figure 18A:
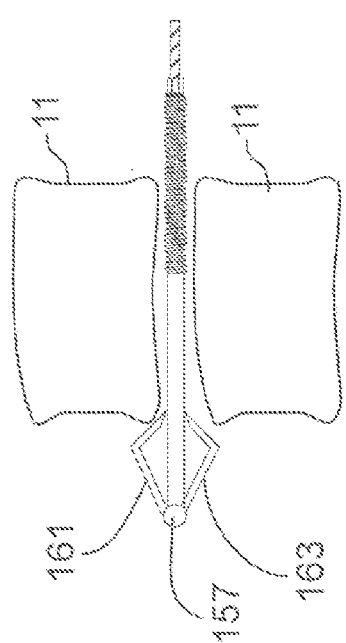
FIG. 18A is a side elevation view of the staple of FIG. 17.
Figure 18B:
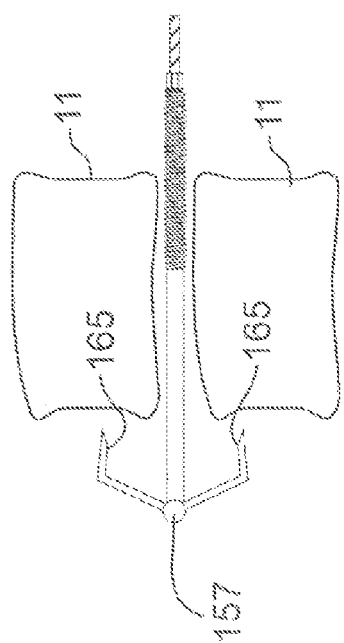
FIG. 18B is a side elevational view.

FIGS. 17-19 show additional features that can be utilized with the present invention. The bone clamp 145 shown in these figures is very similar to the bone clamp shown in FIGS. 13-16. The bone clamp 145 has an elongated rod 147 with a first end 149, second end 151 and a threaded portion 153. A hinge 157 is positioned on the first end 149 of the elongated rod 147. A first plate 161 and a second plate 163 are pivotally connected to the hinge 157. The ends of the first and second plate that are spaced apart from the hinge 147 contain at least one projection 165. The first and second plates have a first position where the first and second plates are disposed substantially parallel to the longitudinal axis of the elongated rod 147. In the second position for the first and second plates the plates are positioned so that they are substantially perpendicular the longitudinal axis of the elongated rod 147. The hinge 157 may contain a biasing means to generally position the first and second plates in the second position. As shown in FIG. 18 the projections 165 can be located on each corner of the first plate 161 and the second plate 163. As shown in FIG. 19, where the first and second plates are narrower, the projections 165 can be positioned substantially in the center of the first and second plates. The first and second plates are of a different length so that the projection 165 on the first plate 161 is not displaced as far from the elongated rod 147 as the projections 165 on the second plate 163 when the first and second plates are in the second position. This construction for the first and second plates allow the projections on the first plate 161 to nest inside of the projections 165 on the second plate 163 when the first and second plates are in the first position. The bone clamp 145 shown in FIGS. 17-19 used in the same manner as the bone clamp 110 shown in FIGS. 13-16. For the sake of brevity the use of the bone clamp 145 will not be repeated as it is clearly understandable based on the prior description.

A cage and vertebral body clamp can be used at a single disk level. In that case it is thought that the vertebral body clamp in combination with the large size of the cage will provide sufficient stability for a fusion to occur without the use of a lateral plate and screws or posterior pedicle screws and rods. Placement of a vertebral body clamp should be faster than putting in a lateral plate with two or four screws in the vertebral bodies or putting in pedicle screws and rods in an entirely different surgical field. In addition the vertebral body clamp should be safer than placing a lateral plate on the two adjacent vertebrae since the staples, unlike the screws for the lateral plate, will be well away from the segmental arteries crossing the mid vertebral bodies laterally. Also, the vertebral body clamps should pose less risk to neural structure than pedicle screws.

Lateral Plating System for Multiple Segment Stabilization and Correction of Scoliosis Including Cables for the Positioning of Plates and Fasteners and Also Motion Preservation Devices Including an Artificial Disk If multiple disk spaces are fused with lateral cages and vertebral body clamps, it may be desirable to reinforce the construct with a lateral plate. A lateral plate extending over two or more disk levels might also be desirable to correct scoliosis beyond the correction achieved with the lateral cages and vertebral body clamps. If vertebral body clamps could not be used at some levels with a lateral cage, then lateral bone screws could be placed in the vertebral bodies above and below the cage for use with a lateral plate A lateral plate 65 is positioned over the flexible cables 61 to position the lateral plate adjacent the spinal fusion cages 10. The flexible cables 61 extend through the elongated opening 67 in the lateral plate 65. The lateral plate 65 is then slid down over the cables and over the threaded rods 35 on the vertebral body clamps or lateral vertebral body screws 85 Lock nuts 53 are then slid down the cables and tightened down on the threaded rods using a vari-angle socket torque wrench guided into position over the lock nut with the cable that is placed through the hollow center of the wrench FIG. 22 (without the cable tensioning parts).

Figure 10:
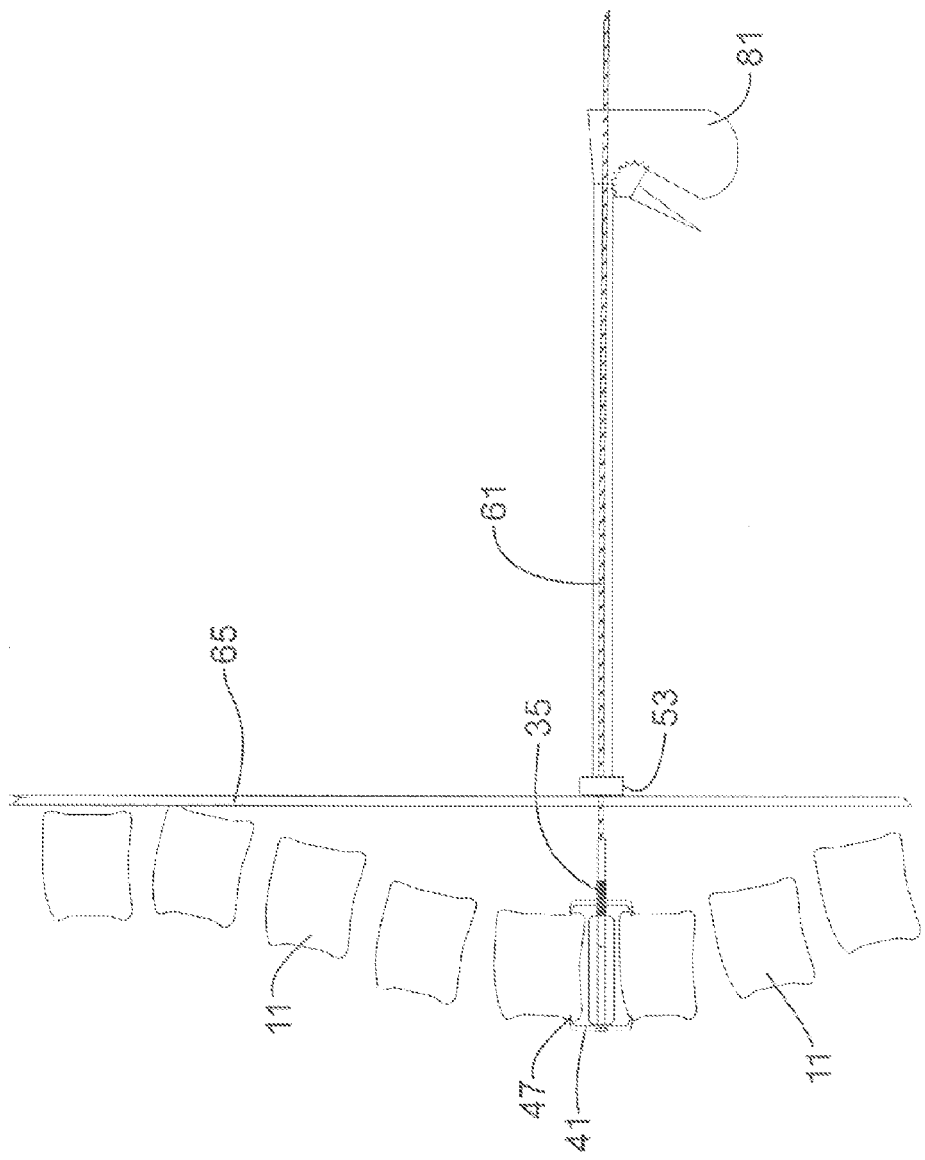
FIG. 10 is a side elevational view.
Figure 22:
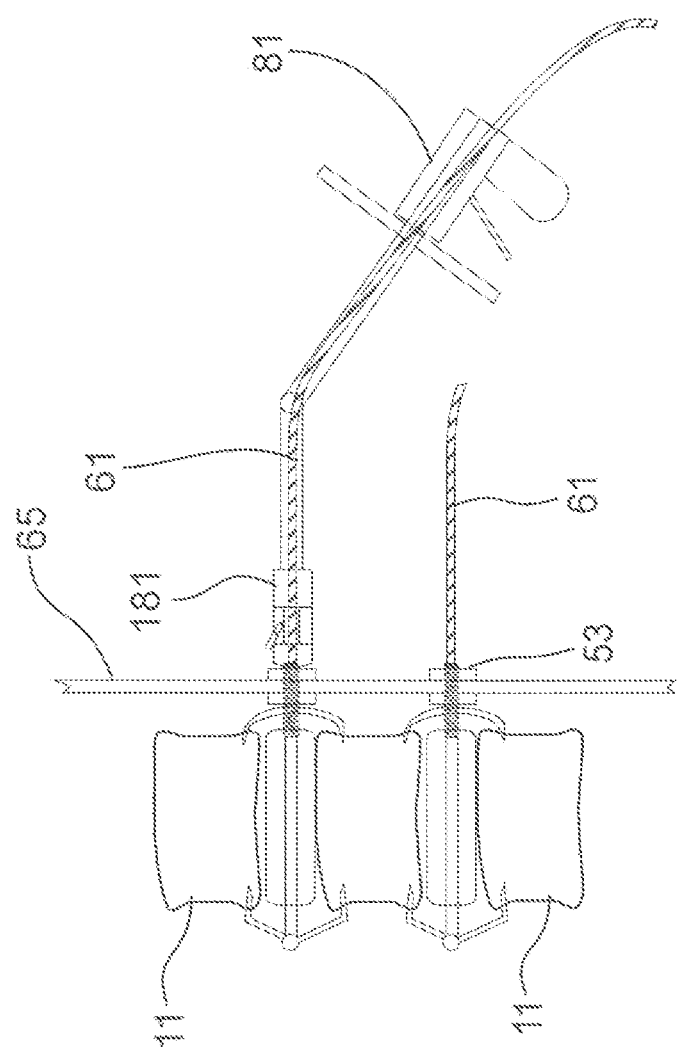
FIG. 22 is a side elevational view of the features of FIG. 21.
Figure 23:
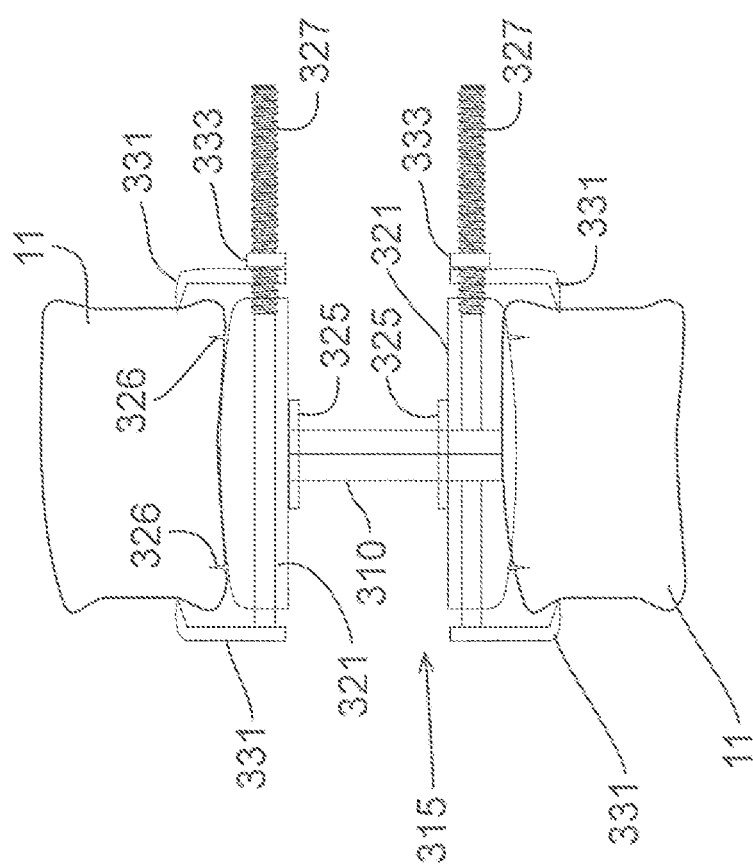
FIG. 23 is a side elevational view of another feature of the invention.
Figure 24:
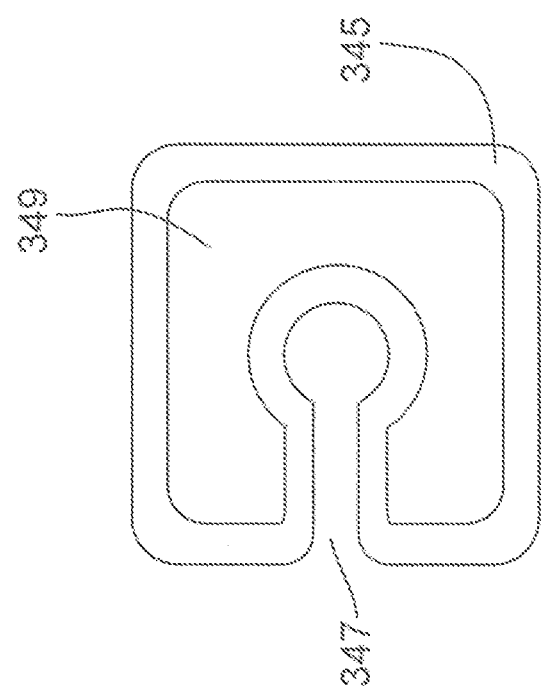
FIG. 24 is a partial top view of the feature of FIG. 23.
Figure 25:
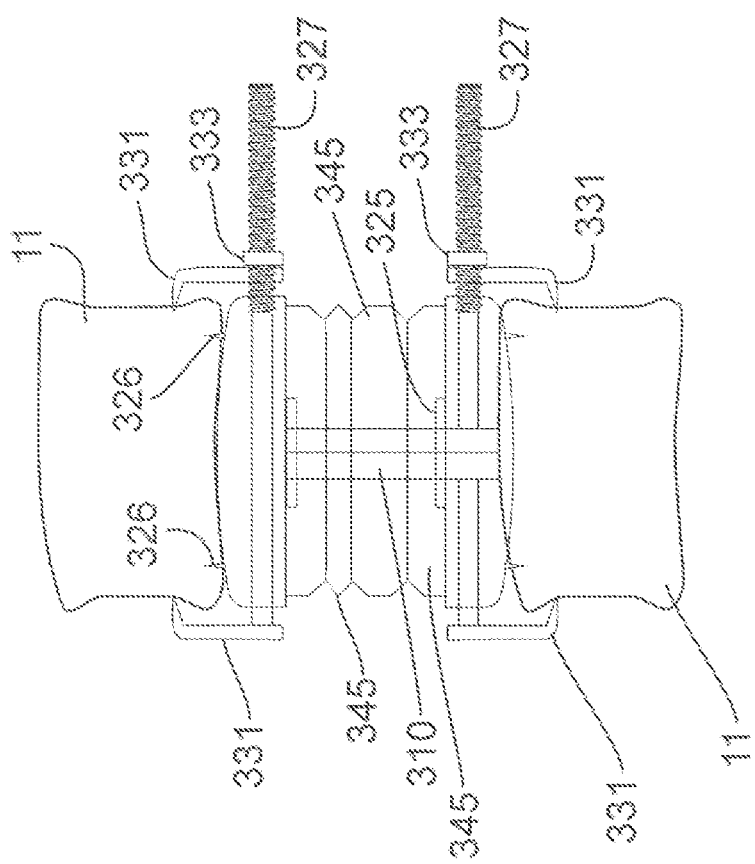
FIG. 25 is a side elevational view of a feature of the invention.

If the spine has a severe scoliotic curvature as shown in FIG. 10 it may not be possible to position the lateral plate 65 directly against the lock nut 53. In this instance it is possible to utilize a vari-angle socket torque driver with a cable tensioning device FIG. 22 (a.k.a. cable tensioning gun with lock nut tightener) in combination with a tensioning lock nut FIG. 21 to pull the flexible cable 61 in a direction to remove the curvature of the spine and to bring the vertebrae 11 into position adjacent the lateral plate 65. The cable tensioning device on the vari-angle socket torque driver with cable tensioning device uses a ratchet mechanism to maintain traction on the cable. A tensioning lock nut FIG. 21 is advanced along the flexible cable 61 and engages the lateral plate 65. The tensioning lock nut FIG. 21 has a releasable cam or pawl 177/179 that secures it in position on the flexible cable 61. A vari-angle socket torque driver with a cable tensioning device FIG. 22 is passed over the cable placing the cable through the hollow center of the driver and tensioning device. The driver/tensioning device is advanced down the cable until the socket engages the nut of the tensioning lock nut FIG. 21. The socket pushes down on a lever arm extending from the cam or pawl releasing it from the cable. The vari-angle socket torque driver with cable tensioning device is then used to pull the cable through the lateral plate 65 and the tensioning lock nut until the lock nut engages the threaded rod on the bone clamp. The lock nut can then be tightened down on the threaded rod and torqued while the vari-angle socket torque driver with cable tensioning device maintains traction on the cable. The tensioning lock nut 175 allows the vari-angle socket driver and cable tensioning device to be switched to another vertebral body clamp if repeated sequential tightening is necessary to correct severe scoliosis. The cam or pawl 177/179 is designed to allow traction to be released if necessary. If scoliosis is not severe, it may be possible to use the vari-angle socket driver/tensioning device FIG. 22 (a.k.a. cable tensioning gun with lock nut tightener) to pull the spine into alignment and put a simple lock nut rather than a tensioning lock nut on the threaded post of the vertebral body clamp or lateral bone screw. Once the vertebrae 11 and lateral plate 65 are in the desired location the portion of the flexible cable 61 that extends beyond the locking clamp 71 can be cut and removed from the patient.

Figure 8:
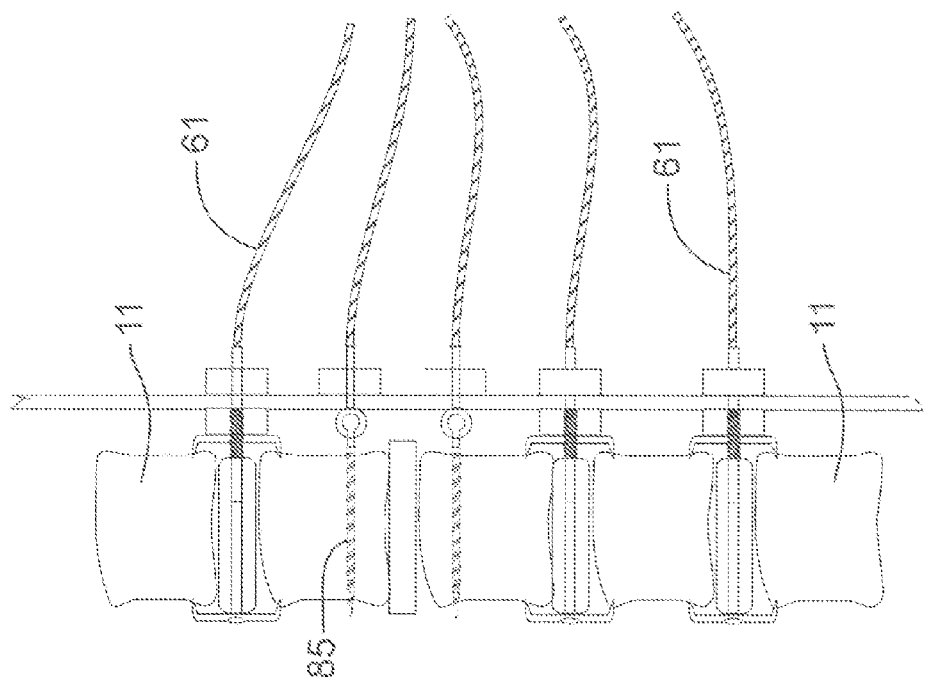
FIG. 8 is a side elevational view of the invention.
Figure 9:
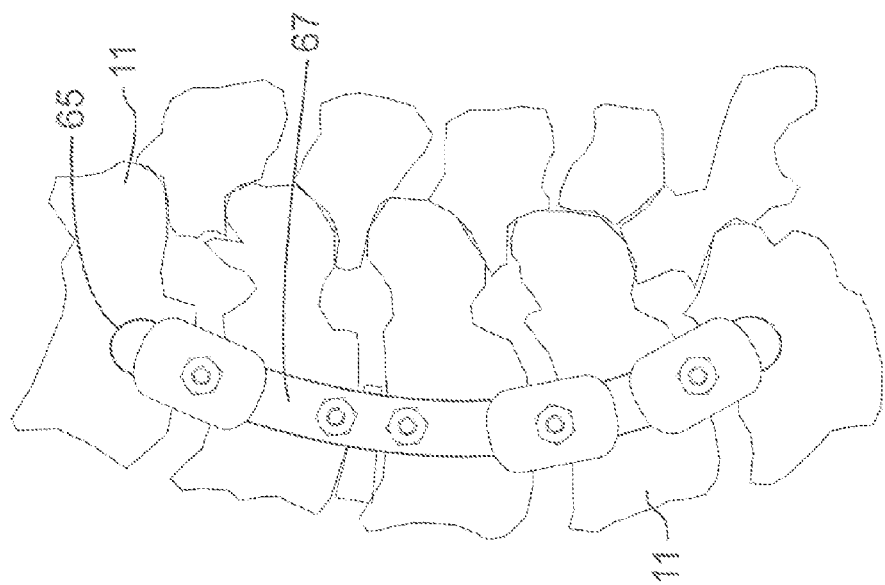
FIG. 9. is a front elevational view of the invention.
Figure 11:
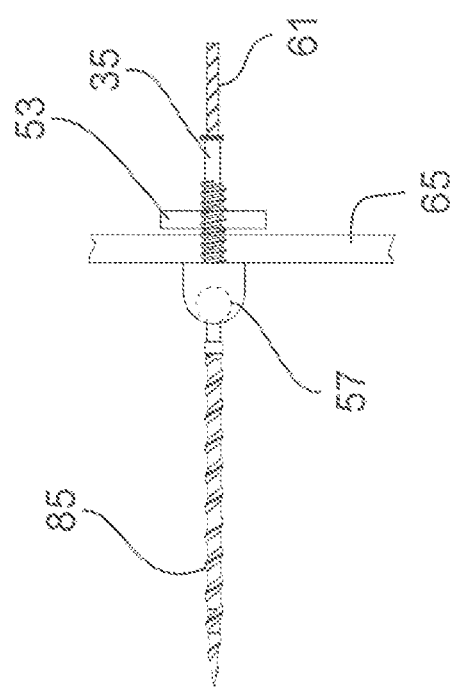
FIG. 11 is a partial side elevational view of an additional feature of the invention.

It is also possible as shown in FIGS. 8 and 11 to use a screw 85 having a flexible cable 61 associated therewith for removing undesirable curvature in the spine. The screw 85 can be advanced into vertebrae 11 when there is no need to replace a disc with a spinal fusion cage 10. A lateral vertebral body screw is put in using the standard technique with an awl to make a pilot hole, a tap and then bicortical placement of the screw. Once the screw 85 is secured in the vertebrae 11 the flexible cable 61 is advanced through the elongated opening 67 in the lateral plate 65. A vari-angle socket torque driver/cable tensioning device FIG. 22 (a.k.a. cable tensioning gun with lock nut tightener) as previously described can then be used to advance the flexible cable 61 in a direction to remove or substantially reduce undesirable curvature in the spine. A lock nut 53 in the socket of the vari-angle socket torque driver/cable tightener can be advanced on to the end of the threaded rod 35 while maintaining traction on the cable that extends through the lateral plate 65 to hold the screw 85 in the desired position wherein the vertebrae 11 are adjacent the lateral plate 65. It is also possible as previously described to use a tensioning lock nut 175 to hold the vertebra against the lateral plate and then screw it on the post of the vertebral body screw. Once the spine is in the desired position adjacent the lateral plate 65 the flexible cable 61 can be cut and removed from the patient.

Figure 6F:
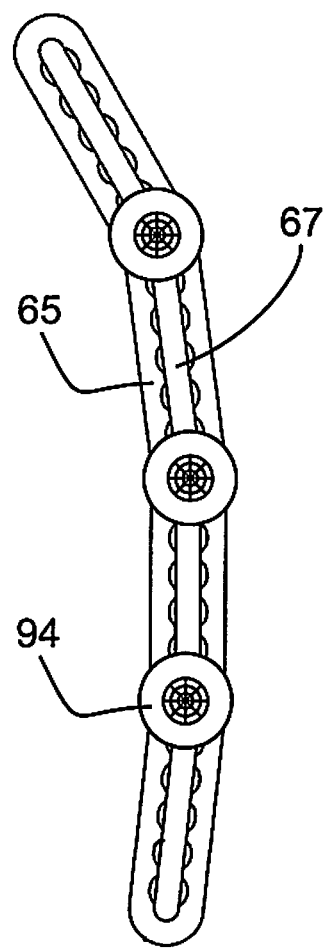
FIG. 6F is a partial side elevational view of another feature of the lateral plates.
Figure 12D:
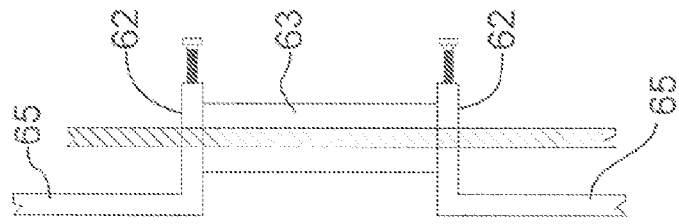
FIG. 12D is a partial side elevational view.
Figure 12C:
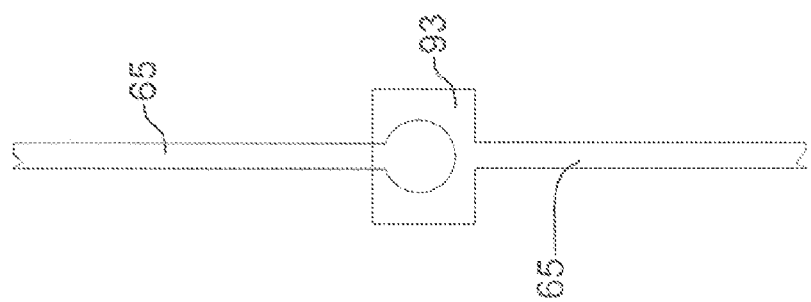
FIG. 12C is a partial side elevational view.
Figure 12B:
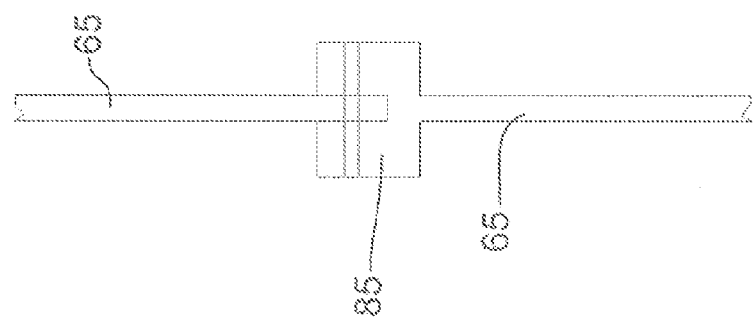
FIG. 12B is a partial side elevational view.
Figure 16:
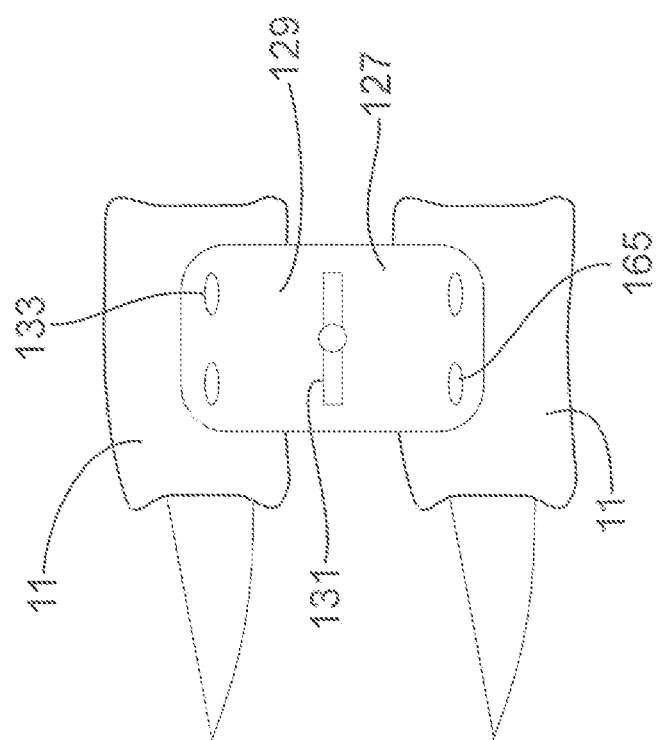
FIG. 16 is an end view of the feature of FIG. 13.

As shown in FIG. 12 it may be necessary to utilize a lateral plate 65 that extends over several vertebrae 11 of the spine. Such a long lateral plate may be difficult to place in the patient without making an overly large incision. In view of the minimally invasive procedures utilized with the spinal fusion cage of the present invention such large incisions are clearly not desirable. To facilitate the positioning of a large lateral plate a hinge 69 can be positioned in one or more locations along the length of the lateral plate. This will allow the lateral plate fold upon itself and to present a smaller size for insertion into the patient. Once the lateral plate is in position near the vertebrae 11 the lateral plate unfolded to extend along the vertebrae 11. A locking plate 87 can be positioned on the lateral plate 65 adjacent the hinge or hinges 69. The locking plate 87 prevents the lateral plate from folding in an undesirable direction. Other hinges are incorporated in the longer lateral plates to allow adjustment of the curvature of the plate in the antero-posterior dimension FIG. 6C. The hinges 94 could be of several designs but a likely design would involve interlocking radially oriented teeth with a central locking screw. These hinges would allow for alteration of the kyphotic or lordotic curvature of the plate to accommodate the curvature of the spine to minimize the number of plates that would need to be available for surgery.

The lateral plate 65 has end 66 that can be designed to mateingly engage other plates 91 that are used to stabilize the spine. The ends 66 can be inserted into receptacles 93 provided on the adjacent plate 91. This allows the elongated plate 65 and the adjacent plate 91 to form a longer stabilization structure for the vertebrae 11 of the spine. This feature could be used to connect a lateral plate on the thoracic spine with one on the lumbar spine allowing two surgeons to work independently, one in the thoracic and the other in the lumbar area and then connect their plates through the diaphragm. This feature also allows for staging of surgery to correct scoliosis in the thoracic and lumbar areas doing either the thoracic or lumbar procedure first and the other at a later time. A variation on this instrumentation and technique would allow a lateral plate to be placed on one side of the spine in the thoracic area and the other side in the lumbar area if this would be better to correct scoliosis. Extensions of the connecting rods of the vertebral body clamps or extensions of vertebral body screws could be used to secure the upper or lower end of a plate on the opposite side of the spine.

The over-all design of this system allows for a variation on the lateral plate that some surgeons might find preferable. This variation involves the use of one, two or more rods FIG. 6B, 91, most likely titanium that could be bent to accommodate various lordotic or kyphotic curvatures of the spine and also bent to accommodate residual scoliosis that could not be corrected or which was thought not appropriate to correct. The bent and cut rods are connected together in a parallel fashion using connecting clamps 92 the two halves of which can be secured with a screw or with the threaded bolt on a vertebral body clamp or vertebral body screw. Variations on the cables and the instruments associated with the cables such as the tensioning lock nut and the vari-angle socket torque driver with a cable tensioning device (a.k.a. cable tensioning device with lock nut tightener) could be used with a rod system in a similar fashion to that described above for a lateral plate. Other devices and techniques used with the plating system such as connecting lateral plates in the thoracic and lumbar areas can be readily adapted to a lateral rod system. A lateral rod system could also be used with the motion preservation devices described below.

Figure 20A:
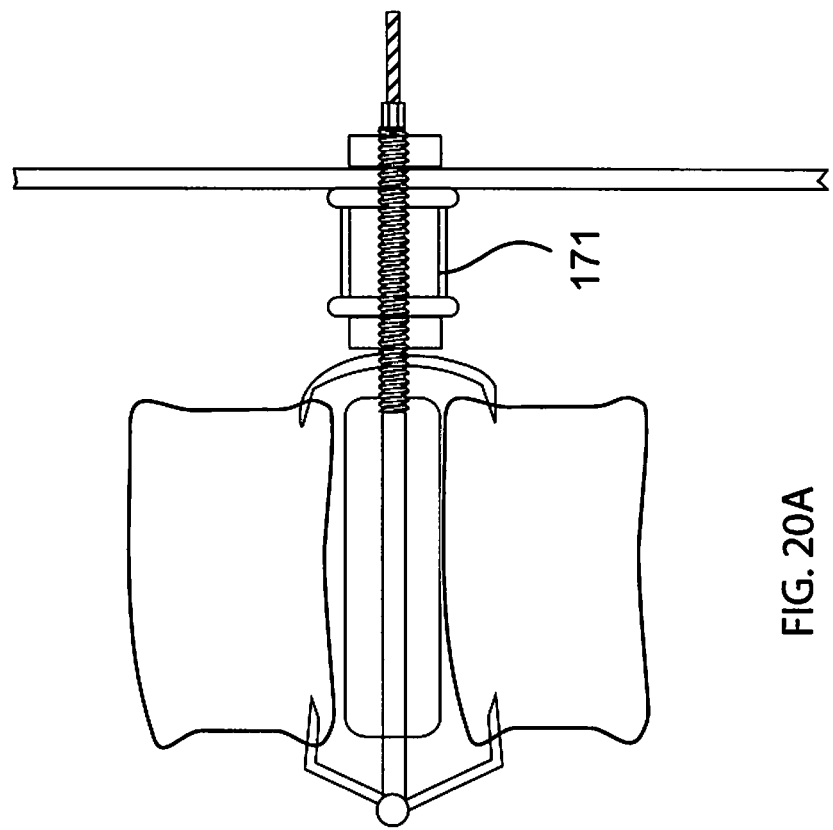
FIG. 20A is a side elevational view of another feature of the invention.
Figure 20B:
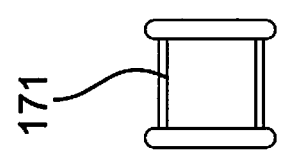
FIG. 20B is a partial side elevational view of the invention.
Figure 20C:
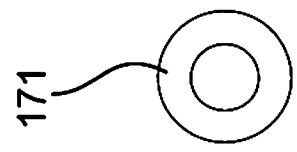
FIG. 20C is a partial end view of the invention.

FIG. 20 shows an additional feature that can be used with the invention. A spacer 171 can be positioned adjacent the lock nut 53. The spacer is used to hold the lateral plate 65 or rods 91 in spaced apart relationship with the vertebrae 11. This position for the lateral plate provides space for the paraspinous muscles that are on the side of the vertebrae. Various sizes would be produced to accommodate various thicknesses of the muscles.

Motion Preservation

Figure 27:
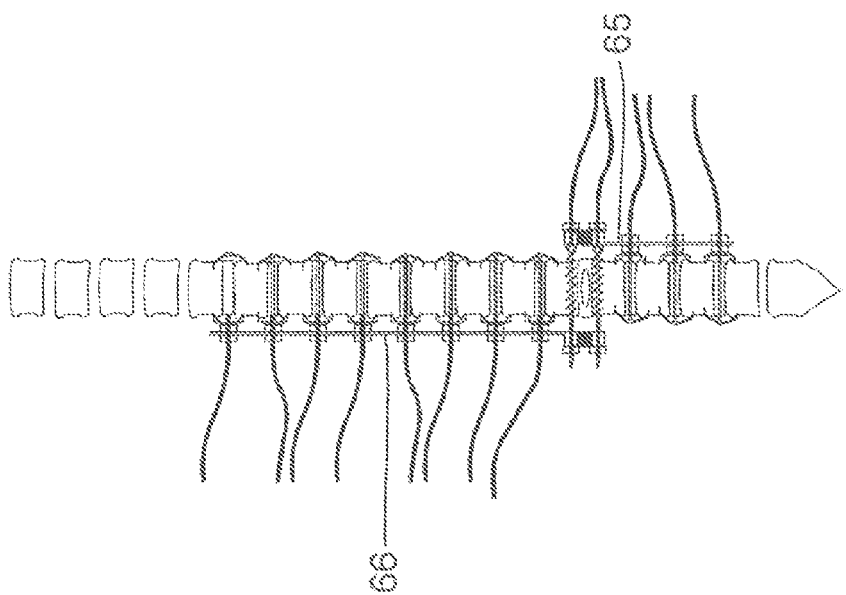
FIG. 27 is a side elevational view of another feature of the invention.

In the event that preservation of some motion in the spine in the process of correcting thoracic and lumbar scoliosis with lateral plates is a consideration, this could be accomplished in several ways. Although several intact disks could reasonably be left between a lateral plate in the thoracic area and one in the lumbar area, a single disk could not be expected to last long because of the increased stress caused by the lever arms of the lateral plates above and below. A single disk could be reinforced with flexible connectors placed lateral to it and attached to bone clamps in the disk spaces above and below. Staples or lateral plates 65 above and below the disk to be preserved can be joined together by a tube and cable that extends between the adjacent lateral plates. A flange 62 can be positioned on each lateral plate and a plastic tube 63 made of polycarbonate urethane or other material can be cut to the appropriate length and secured between the flanges with a polyethelene-terephalate cable 64 that can be tensioned with the previously described cable tensioner and secured to the flanges with set screws. At the time of a second operation to place a second lateral plate 66, as shown in FIG. 27 on the opposite side in the thoracic or lumbar area, flanges can be placed on extensions of the center bolt of the vertebral body clamps. A tube can then be cut and secured with a cable that is tensioned and secured with set screws. Alternate types of flexible disk supports would be a hinge FIG. 12B or ball and socket FIG. 12C.

In the event that some motion preservation between thoracic and lumbar plate constructs is thought beneficial but the disks in the thoraco-lumbar area appear to be too degenerated to hold up, a laterally inserted artificial disk secured to the vertebrae and lateral plates with vertebral body clamps can be utilized to preserve some motion in the spine between the rigid areas above and below. The articulating portion of the artificial disk would be of a conventional dome and groove design allowing a slight amount of translation in forward flexion. The articulating surfaces would be either metal on metal or metal on plastic. The upper and lower plates would include a through bolt attached to a staple (lateral plate) on each side. Once the disk material is removed leaving the anterior and posterior annulus and longitudinal ligaments intact, the artificial disk is positioned from a lateral approach and clamped to the vertebrae above and below. Lateral plates can then be attached to the top and bottom plates of the disk.

Figure 28:
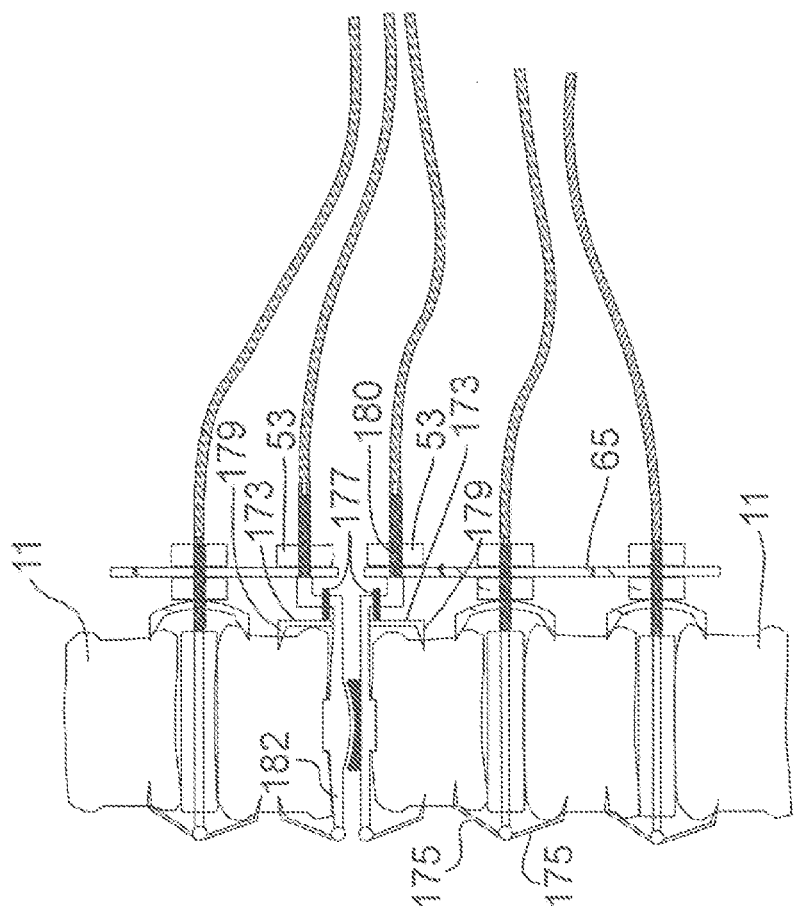
FIG. 28 is a side elevational view of another feature of the invention.
Figure 29:
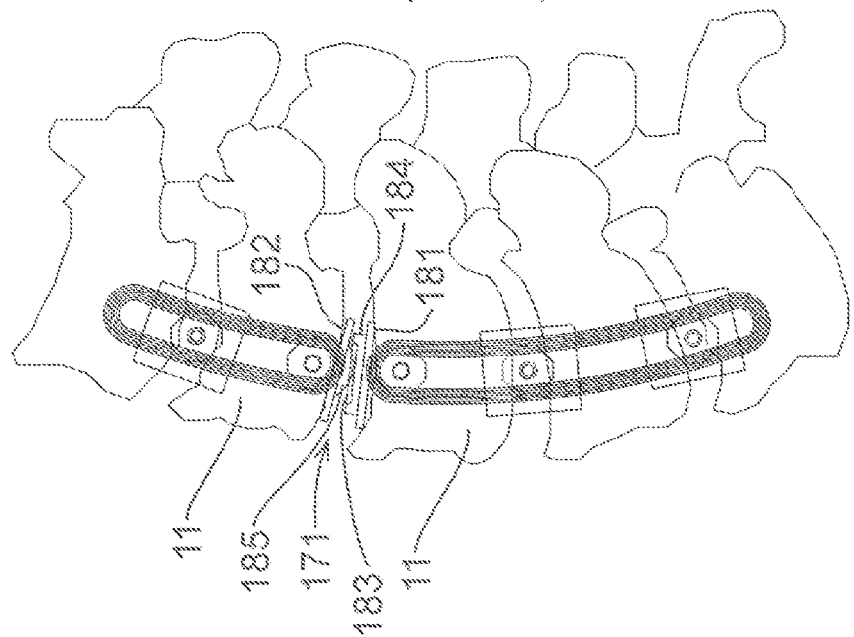
FIG. 29 is an end view of the feature of FIG. 28.
Figure 30:
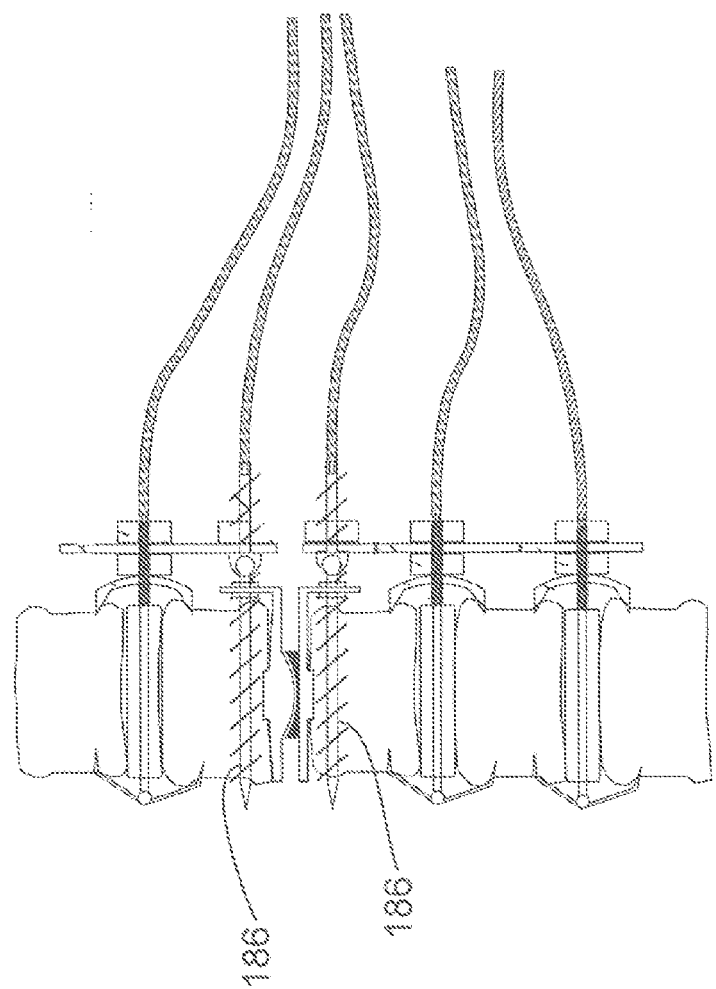
FIG. 30 is a side elevational view of another feature of the invention.

As shown in FIGS. 28 and 29 the artificial disk 171 is positioned in the space between adjacent vertebrae. The artificial disk is attached to clamps 173 similar to the clamps previously described. The clamps have a foldable staple 175 on one end that is connected to a rod 177. A fixed staple 179 is positioned on the opposite end of the rod. The fixed staple is advanced toward the vertebrae 11 by a lock nut 53 that is positioned on a threaded rod 180 that extends from the fixed staple 179. A lateral plate 65 can be positioned between the fixed staple and the lock nut. The foldable staple is advanced to engage the vertebrae by rotation of the rod 177. A first plate 181 and a second plate 182 are positioned in the space in opposed relationship. The first and second plates are positioned on the rods 177 that are secured by adjacent vertebrae by the clamps 173. The first plate defines a recess 183 and a groove 184 can be positioned in the recess. The second plate 181 has a semicircular ball 185 that extends from the second plate to engage the recess 183. The ball 185 can rotate or pivot in the recess to provide motion in the spine between adjacent vertebrae 11 in a manner similar to a disk normally present in the spine. The groove 184 can assist in providing movement of the ball and for retaining the ball in the desired location in the recess. FIG. 30 shows another feature of an artificial disk where the first and second plates are held in position by screws 186 instead of the previously described clamps. The screws function in the manner previously described to secure the first and second plates to the adjacent vertebrae 11.

Self-Stabilized Intervertebral Body Fusion Cage Incorporating Vertebral Body Clamps and Stackable Spacers for Use after Thoracic or Lumbar Corpectomy with a Minimally Invasive Approach FIGS. 23-26 show an additional feature of the invention. In some spinal injuries, one or more vertebrae are fractured and damaged to an extent that the vertebrae must be removed. Removal of vertebrae leaves a significant space or gap in the spine and it is necessary to hold or maintain this space when repairing the spine. To maintain this space an expandable support post 310 can be positioned in the space 315 between adjacent vertebrae 11. The expandable support post is connected to a support plate 321 on each end of the support post. The support plates are designed to engage the adjacent vertebrae 11 and are substantially as wide and long as the vertebrae. At least one projection 326 can be positioned on the support plates. The projections are disposed to engage the vertebrae and assist in holding the support plates in the desired position relative to the vertebrae. A hinge joint 325 can be used to secure the support plates. The hinge joint allows the support plates to pivot or rotate relative to the expandable support post to accommodate adjacent vertebrae that are not in parallel alignment. A threaded rod 327 and a staple 331 are secured to each end of the threaded rod. A lock nut 333 is positioned on the thread rod and is used to advance the staples into engagement with the vertebrae to secure the support post 310 in the desired location relative to the adjacent vertebrae. Frequently the support post 310 is positioned in the space 315 in a collapsed orientation to facilitate positioning the support post in the space. Once the support post is properly positioned, it is expanded until the support plates 321 are in engagement with the adjacent vertebrae 11. Once the support plates are positioned the lock nut is advanced to cause the staples 331 to engage the vertebrae 11 and hold the support plates 321 in the desired position with respect to the vertebrae 11.

Figure 26:
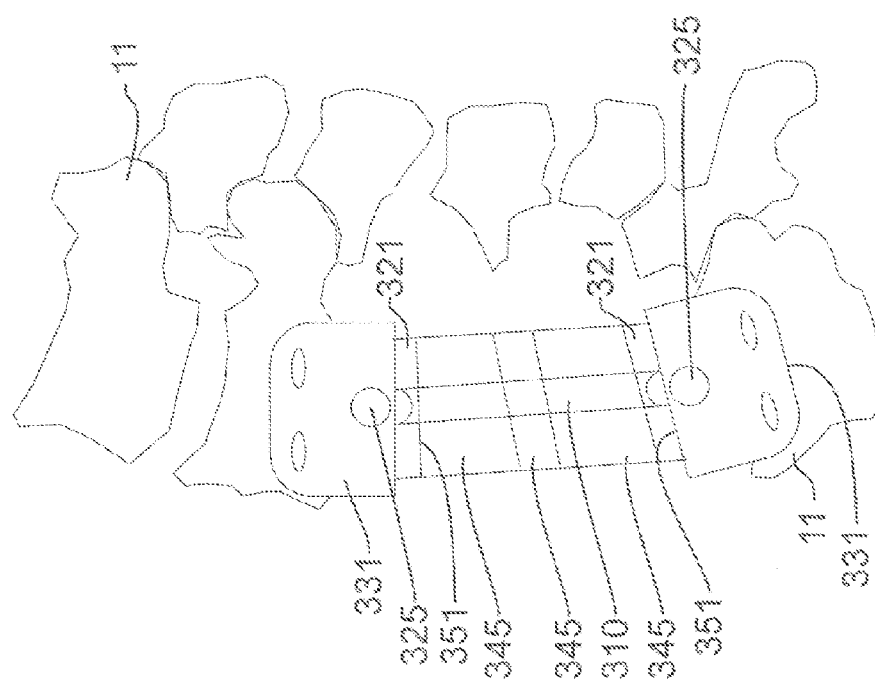
FIG. 26 is a side elevational view of a feature of the invention.

Spacers 345 can then be inserted into the space 315 to provide additional support for the adjacent vertebrae. The spacers 345 have a passageway 347 that allows the spacers to fit around the expandable support post 310. The spacers have a hollow interior 349 to allow for bone or bone growth material to be positioned in the spacers. The bone growth material allows the spacers to become integrally connected with the adjacent vertebrae. The spacers 345 can have different heights to accommodate or fill spaces 315 of varying size. The spacers can also have angled surfaces 351 as shown in FIG. 26 to accommodate different orientation between the adjacent vertebrae.

As shown in FIGS. 28 and 29 the artificial disk 171 is positioned in the space between adjacent vertebrae. The artificial disk is attached to clamps 173 similar to the clamps previously described. The clamps have a foldable staple 175 on one end that is connected to a rod 177. A fixed staple 179 is positioned on the opposite end of the rod. The fixed staple is advanced toward the vertebrae 11 by a lock nut 53 that is positioned on a threaded rod 180 that extends from the fixed staple 179. A lateral plate 65 can be positioned between the fixed staple and the lock nut. The foldable staple is advanced to engage the vertebrae by rotation of the rod 177. A first plate 181 and a second plate 182 are positioned in the space in opposed relationship. The first and second plates are positioned on the rods 177 that are secured by adjacent vertebrae by the clamps 173. The first plate defines a recess 183 and a groove 184 can be positioned in the recess. The second plate 181 has a semicircular ball 185 that extends from the second plate to engage the recess 183. The ball 185 can rotate or pivot in the recess to provide motion in the spine between adjacent vertebrae 11 in a manner similar to a disk normally present in the spine. The groove 184 can assist in providing movement of the ball and for retaining the ball in the desired location in the recess. FIG. 30 shows another feature of an artificial disk where the first and second plates are held in position by screws 186 instead of the previously described clamps. The screws function in the manner previously described to secure the first and second plates to the adjacent vertebrae 11.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A spinal fusion cage comprising:
    a spinal cage configured to be positioned in an intervertebral space between adjacent vertebrae, the spinal cage having opposed lateral sides;
    at least one passageway disposed in the spinal cage and extending from one lateral side of the spinal cage to the opposite lateral side of the spinal cage;
    a threaded rod positioned in the at least one passageway, the threaded rod extending beyond the lateral sides of the spinal cage;
    a staple having a base and two spaced apart points extending from the base, a staple rotatably positioned on the threaded rod adjacent each of the opposed lateral edges of the spinal cage; the staples being disposed to have the spaced apart points engage the vertebrae above and below the spinal cage;
    a lock nut positioned on the threaded rod on the side of one of the staples that is spaced apart from the spinal cage whereby rotation of the threaded rod will advance the staples to cause the staple to engage the vertebrae above and below the cage whereby the staples assist in positioning the spinal cage in the spine.

2. The cage of claim 1 wherein the spaced apart points of the staples contain an aperture, the aperture being disposed to allow bone to grow through the aperture to assist in securing the staple in the vertebrae.

3. The cage of claim 1 wherein the lock nut engages the staple positioned on the threaded rod, the lock nut placing a biasing force on the staple as the threaded rod is rotated.

4. The cage of claim 1 wherein the spaced apart points of the staples are disposed to be in engagement with the spinal cage when the cage is positioned in the intervertebral space between adjacent vertebrae.

5. The cage of claim 4 wherein the staples are rotated by the rotation of the threaded rod to bring the spaced apart points of the staples into alignment with the vertebrae above and below the spinal cage.

6. The cage of claim 5 wherein the threaded rod has a cross sectional shape that engages the base of the staples whereby rotation of the threaded rod rotates the staples to position the spaced apart points of the staples into alignment with the vertebrae above and below the spinal cage.

7. The cage of claim 3 wherein a drive head is positioned on the end of the thread rod that is adjacent the lock nut.

8. The cage of claim 7 wherein the drive head has a variable angle design whereby the drive head can be engaged at various angles to rotate the threaded rod.

9. The cage of claim 1 wherein a flexible cable is attached to the threaded rod, the cable being disposed to apply lateral force to the cage to adjust the alignment of the vertebrae.

10. The cage of claim 9 wherein a plate is positioned adjacent the cage, the plate being designed to engage at least one vertebrae above and below the cage, the plate having at least one alignment aperture, the alignment aperture being disposed to receive the flexible cable.

11. The cage of claim 10 wherein an advancement device can be connected to the flexible cable to advance the cable towards the advancement device to bias the spinal cage in a direction to align the vertebrae in a desired orientation.

12. The cage of claim 11 wherein the plate has a plurality of apertures, the plurality of apertures being disposed to receive flexible cables attached to threaded rods associated with different vertebrae in the spine, whereby the flexible cables can be advanced by the advancement device to align the vertebrae.

13. The cage of claim 12 wherein a gripping device is positioned on the flexible cables to hold the flexible cables in a desired position with respect to the plate.

14. The cage of claim 13 wherein the gripping device is a pivoting, one way clamp.

15. The cage of claim 14 wherein the gripping device is a lock nut that contains a pawl that engages and retains the cable in the desired position.

16. The cage of claim 15 wherein the pawl is released by a socket placed on the lock nut to rotate the lock nut.

17. The cage of claim 12 wherein the plate has a hinge that allows the plate to be folded to reduce the size of the plate for insertion adjacent the spinal cage, the hinge allowing the plate to be positioned at an angle to accommodate for curvature of a patient's spine.

18. The cage of claim 12 wherein the plate is made of two or more rods that are disposed adjacent the cage.

19. The cage of claim 18 wherein the rods have a hinge that allows the rods to be folded for insertion adjacent the spinal cage, the hinge allows the rods to be positioned at an angle to accommodate for curvature of a patient's spine.

20. The cage of claim 12 wherein a ball and socket system is used to connect two or more adjacent plates, the ball and socket system used to move the plates.

21. A support structure for replacing a vertebrae in a spine, the spine having a vertebrae adjacent each side of the vertebrae that is being replaced comprising:
    a first support plate and a second support plate, the first and second support plates being disposed in spaced apart relationship;

an adjustable length post extending between the first and second plates, the post designed to fit between vertebrae in the spine and then adjusting in length to place the first plate into contact with the vertebrae adjacent one side of the vertebrae that is being replaced and the second plate into contact with the vertebrae adjacent the other side of the vertebrae that is being replaced;

a clamp operatively connected to the first and second plates for securing the first and second plates to the vertebrae adjacent the vertebrae that is being replaced.

22. The support structure of claim 21 wherein a first threaded rod is operatively connected to the first plate and a second threaded rod is operatively connected to the second plate, at least one staple being positioned on the first and second threaded rods causes the staple to engage a vertebrae adjacent the vertebrae that has been removed, the at least one staple securing the first plate to one vertebrae and the second plate to the opposed vertebrae that has been removed.

23. The support structure of claim 22 wherein at least 2 staples are positioned on the first and second rods, the at least two staples engaging the vertebrae to secure the first and second plates in position in the space where the vertebrae has been removed.

24. The support structure of claim 21 wherein at least one projection is positioned on a side of the first and second plates that engages the vertebrae, the at least one projection engaging the vertebrae to assist in securing the first and second plates in position with respect to the vertebrae.

25. The support structure of claim 21 wherein at least one spacer is positioned around the adjustable length post to retain the desired space between the first and second plates.

26. The support structure of claim 25 wherein the at least one spacer has a hollow interior to accommodate bone growth material.

27. The support structure of claim 25 wherein the at least one spacer has a passageway that is designed to fit around the adjustable length post.

28. The support structure of claim 21 wherein the first and second support plates are pivotably secured to the adjustable length post.

29. An artificial disk for positioning between adjacent vertebrae in a spine comprising:
a first plate disposed adjacent one of the adjacent vertebrae;
a second plate disposed adjacent the other adjacent vertebrae;
a clamp operatively connected to each of the first and second plates, the clamps engaging the opposed vertebrae to secure the first plate to one of the adjacent vertebrae and the second plate to the other adjacent vertebrae;
a recess defined in the first plate;
a projection extending from the second plate, the projection designed to be moveably positioned in the recess, the projection allowing relative movement between the adjacent vertebrae.

30. The artificial disk of claim 29 wherein the clamp has a staple at each end, the staple at each end of the clamp being designed to engage the adjacent vertebrae to secure the first and second plates to the adjacent vertebrae.

* * * * *